US012742201B2

(12) United States Patent
Ost

(10) Patent No.: US 12,742,201 B2
(45) Date of Patent: Sep. 22, 2026

(54) METHODS FOR THE MULTIPLEXED ISOTHERMAL AMPLIFICATION OF NUCLEIC ACID SEQUENCES

(71) Applicant: DNAE DIAGNOSTICS LIMITED, London (GB)

(72) Inventor: Toby Ost, London (GB)

(73) Assignee: DNAE DIAGNOSTICS LIMITED, London (GB)

( * ) Notice: Subject to any disclaimer, the term of this patent is extended or adjusted under 35 U.S.C. 154(b) by 872 days.

(21) Appl. No.: 17/632,705

(22) PCT Filed: Aug. 7, 2020

(86) PCT No.: PCT/GB2020/051890
§ 371 (c)(1),
(2) Date: Feb. 3, 2022

(87) PCT Pub. No.: WO2021/028665
PCT Pub. Date: Feb. 18, 2021

(65) Prior Publication Data

US 2023/0183792 A1 Jun. 15, 2023

(30) Foreign Application Priority Data

Aug. 9, 2019 (GB) ..................................... 1911421

(51) Int. Cl.
*C12Q 1/6855* (2018.01)

(52) U.S. Cl.
CPC ....... *C12Q 1/6855* (2013.01); *C12Q 2600/16* (2013.01)

(58) Field of Classification Search
None
See application file for complete search history.

(56) References Cited

U.S. PATENT DOCUMENTS

2008/0318282 A1 12/2008 Uematsu et al.
2017/0145492 A1 5/2017 Pham et al.

FOREIGN PATENT DOCUMENTS

| | | | | |
|---|---|---|---|---|
| CN | 105821138 B | | 5/2018 | |
| JP | 2009000044 A | | 1/2009 | |
| WO | WO-2004072294 A2 | * | 8/2004 | ........... C12Q 1/6869 |
| WO | WO-2012103154 A1 | * | 8/2012 | ........... C12Q 1/6806 |
| WO | 2014071322 A1 | | 5/2014 | |
| WO | 2015157747 A1 | | 10/2015 | |
| WO | WO-2019073049 A1 | * | 4/2019 | ........... C12Q 1/6844 |

OTHER PUBLICATIONS

International Search Report and Written Opinion issued on Sep. 30, 2020, in corresponding to International Application No. PCT/GB2020/051890; 16 pages.

Tsugunori Notomi et al., “Loop-mediated isothermal amplification of DNA”; Nucleic Acids Research, Information Retrieval Ltd., vol. 28; No. 12; Jan. 1, 2020; pp. E6301-E63.7; XP003018858; ISSN: 0305-1048.

Combined Search and Examination Report dated Jan. 20, 2020, in corresponding to German Application No. 1911421.4; 6 pages.

Office Action issued on May 21, 2024, in corresponding Japanese Application No. 2022-507905, 11 pages.

* cited by examiner

*Primary Examiner* — Carolyn L Greene

(74) *Attorney, Agent, or Firm* — Maier & Maier, PLLC

(57) ABSTRACT

A method for the isothermal amplification of nucleic acid molecules, optionally on a solid support. The method uses single stranded nucleic acids having hairpin regions at both the 3' and 5' ends, or the extension products thereof.

4 Claims, 17 Drawing Sheets

Specification includes a Sequence Listing.

P2_del solution LAMP primer
5'
LP2
LP2'
5'
3'

| LANE | 01 | 02 | 03 | 04 | 05 | 06 | 07 |
|---|---|---|---|---|---|---|---|
| Ladder | + | | | | | | + |
| LAMP_PhiX_* | | 01 | 02 | 03 | 04 | 05 | |
| PCR_F (SBL_PHIX_*) | | 01 | 03 | 05 | 07 | 09 | v1 |
| PCR_R (SBL_PHIX_*) | | 02 | 04 | 06 | 08 | 10 | |
| Insert size bp | | 228 | 188 | 186 | 189 | 222 | |
| Expected amplicon bp | | 331 | 291 | 289 | 292 | 325 | |

300 bp
200 bp
150 bp
100 bp
75 bp
50 bp
25 bp

3% TBE agarose gel

FIG. 14

| LANE | 01 | 02 | 03 | 04 | 05 | 06 | 07 | 08 | 09 | 10 | 11 | 12 | 13 | 14 | 15 |
|---|---|---|---|---|---|---|---|---|---|---|---|---|---|---|---|
| Ladder | + | | | | | | | | | | | | | | + |
| Insert (SHRK_INS01) | | + | - | - | + | + | + | + | + | + | + | + | + | + | |
| LP1 adapter | | - | V1 | V2 | V1 | - | V2 | - | V1 | V2 | V1 | V2 | V1 | V2 | |
| LP2 adapter | | - | V1 | V2 | - | V1 | - | V2 | V1 | V2 | V1 | V2 | V1 | V2 | |
| Ligase | | - | - | - | + | + | + | + | + | + | - | - | + | + | |
| Correct primers | | + | + | + | + | + | + | + | + | + | + | + | - | - | |
| Incorrect primers | | - | - | - | - | - | - | - | - | - | - | - | + | + | |
| LAMP mix | | + | + | + | + | + | + | + | + | + | + | + | + | + | |

3% TBE agarose gel

FIG. 16

| LANE | 1 | 2 | 3 | 4 | 5 | 6 | 7 | 8 | 9 | 10 | 11 | 12 | 13 | 14 | 15 | 16 | 17 | 18 | | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| Ladder | + | | | | | | | | | | | | | | | | | + | | + | | | | | | | | | | | + |
| Insert (SBL_T0*) | | 1 | 2 | 3 | 4 | 5 | 6 | 7 | - | - | - | - | - | - | - | - | - | - | | | 1 | 2 | - | - | 1 | 2 | 1 | 2 | + | + | |
| 1xE* Ligated LAMPlate (7plex) copies | | - | - | - | - | - | - | - | 7 | 7 | 8 | 8 | 9 | 9 | 8 | 8 | - | | | | - | - | - | - | - | - | - | - | - | - | |
| LAMP amplification mix | | + | + | + | + | + | + | + | + | + | + | + | + | + | - | - | + | | | | + | + | + | + | + | + | + | + | + | + | |
| Bst | | | | | | | | | | | | | | | | | | | | | | | | | | | | | | | |
| Primers | | + | + | + | + | + | + | + | + | + | + | + | + | + | + | - | + | | | | + | + | + | + | + | + | + | + | + | + | |
| Adapters only (LP1_v1 and LP2_v1) | | - | - | - | - | - | - | - | - | - | - | - | - | - | - | - | - | | | | - | - | + | + | - | - | - | - | + | + | |
| LP1-mono SBL_T01_v1 | | - | - | - | - | - | - | - | - | - | - | - | - | - | - | - | - | | | | - | - | - | - | + | + | - | - | - | - | |
| LP2-mono SBL_T01_v1 | | - | - | - | - | - | - | - | - | - | - | - | - | - | - | - | - | | | | - | - | - | - | - | - | + | + | - | - | |
| T4 ligase | | + | + | + | + | + | + | + | + | + | + | + | + | + | + | + | - | | | | + | + | + | + | + | + | + | + | - | - | |

METHODS FOR THE MULTIPLEXED ISOTHERMAL AMPLIFICATION OF NUCLEIC ACID SEQUENCES

REFERENCE TO A SEQUENCE LISTING

In accordance with 37 CFR § 1.821, the present specification makes reference to a Sequence Listing submitted electronically as a .txt file named "Corrected Seq Listing.txt". The .txt file was generated on Jul. 27, 2022, and is 8,363 bytes in size. The entire contents of the Sequence Listing are hereby incorporated by reference.

FIELD

Disclosed is a method for the isothermal amplification of nucleic acids. Disclosed are constructs, methods and kits allowing a form of loop mediated amplification which can be carried out either in solution or on a solid support.

BACKGROUND

Loop-assisted isothermal amplification (LAMP) is a technique first reported by Notomi et al in 2000 (Nucleic Acids Res. 2000; 28 (12):E63.) and is a rapid and efficient method for the isothermal amplification of nucleic acid. The technique employs a strand-displacing DNA polymerase (typically Bst 2.0 WarmStart® DNA Polymerase) and a set of 4 specific oligonucleotide primers designed to six distinct regions of the target template DNA and is typically able to faithfully amplify low template input amounts to ca. $10^9$ copies within short reaction times (e.g. 60 minutes at 65° C.).

LAMP has been used as the basis for numerous diagnostic assays for a variety of infections and diseases due to its sensitivity, specificity and rapid time to result. Being an isothermal method means that it can be used in the field without the requirement for sophisticated thermocycling equipment and is ideally suited to point-of-care applications.

Methods for next generation nucleic acid sequencing may involve amplification of a large number of sequences in parallel. The amplification is often done on a solid support or population of beads such that strands of different sequence are amplified in physical isolation, so called clonal amplification.

LAMP has several features that make it attractive as a clonal amplification method, namely: High amplification speed; Generating multiple copies of the input template as fast as possible is paramount. The absolute copy number per parent template molecule is also key to maximise detection signal.

Isothermal process; This simplifies the workflow and cartridge-ability of the components. Does not require sophisticated thermocycling hardware to run assay.

High fidelity; Ensures that the amplification produces a plurality of features that, when sequenced, reflect the identity of the starting template as well as possible.

Low complexity reaction; Few reaction components required to support amplification ensures robust and reproducible performance.

Low cost of goods; The method is inexpensive to implement.

However conventional LAMP has several disadvantages that make it unattractive as a clonal amplification method, namely:

Difficult and complex to multiplex samples and loci in single tube reactions; As each amplicon requires a unique set of 4 primers, LAMP reactions are typically limited to single-plex or duplex assays. Increasing the plex of a single reaction increases the risk of mis-priming and off-target amplification. The only other practical way to multiplex conventional LAMP is to run multiple, different single-plex reactions in parallel.

Typically, the progress of LAMP amplifications or the product of LAMP reactions are detected by real-time or end-point methods (typically turbidity or an increase in fluorescence with amplification). Whilst LAMP products are amenable to DNA sequencing techniques, due to their low multiplex-ability and their typical use in low-cost assays, their use in combination with DNA sequencing is limited to confirmation of correct amplification and not using DNA sequencing per se as a diagnostic read-out.

The product of LAMP amplification are high-molecular weight structures formed from several inverted repeat concatemeric copies of the patent template strand. These can be linear or, more complex, branched, cauliflower-like structures depending on reaction conditions.

Whilst a variety of LAMP amplification detection methods exist these tend to rely on detection of real-time or end-point solution-amplification products. No report to date has used LAMP to generate surface-bound isothermal amplification.

The inventors of the current invention have devised means to enable a loop-mediated amplification both in solution and on a solid support.

SUMMARY

The inventors have developed an improved isothermal amplification method. The method works both in solution and on a surface, thereby making it amenable as a clonal amplification method, and in doing so retained many of the beneficial features, and remedied many of the negative features, encountered in solution-LAMP isothermal amplification.

The method relies on a single stranded nucleic acid molecule engineered to contain a hairpin region at both the 3' and 5' ends. The 3' ends of the hairpins are able to undergo polymerase extension, thereby making a double stranded material having one terminus which is an 'open' blunt end, linked by a central hairpin. Thus the material being amplified, under fully denaturing conditions, is a single stranded molecule having both sense and antisense strands linked together via a central adaptor with adaptors also at both the 5' and 3' ends, the adaptors at the ends being complementary.

When in double stranded form, the 3' ends are blunt ended, so have no template. When in single stranded form, the ends are self-complementary and can thus self-prime. The amplification is performed using primers which hybridise to the central loops, and thereby extend half the strand. The first primer extension thereby gives material having one half double stranded and one half single stranded. The single stranded 3' end can self-prime, thereby producing a molecule which duplicates the double stranded product. The double stranded concatamer again has one terminus which is an 'open' blunt end, linked by a central hairpin, also having central known double stranded adaptor regions.

Hybridisation of a primer to the central loop and extension thereof again produces a molecule in which half the strand is single stranded and half is double stranded. Again the 3' end of the single stranded region can self-anneal and extend. In such a way, using primers complementary to the single stranded loops and self-extension of the released 3'-ends, concatameric amplification can be achieved. For each 'cycle', the molecule effectively doubles in length as the 3' end produced by the polymerase as the displaced strand can produce a copy of the whole strand.

By immobilising one of the primers on a solid support, as described herein, clonal amplification can be achieved.

BRIEF DESCRIPTION OF THE FIGURES

FIG. 14: Non-denaturing agarose gel image shows the 5 individual loci-specific PhiX-174 PCR amplicons using looped-PCR primers, clean bands show the amplification of products of the expected molecular weight. Lane 1 and 7 are molecular weight ladders. Lane 2-6 are amplicons for regions LAMP_PhiX_01-05. The 5' loops of the PCR_F and PCR_R primers add an additional 103 nt onto the insert length hence the expected shift in molecular weight over the anticipated amplicon insert length.

FIG. 16: Solution LAMP amplification of a single LAMPlate prepared by ligation Non-denaturing agarose gel image shows the pattern of bands typical of LAMP amplification of various single LAMPlicon constructs. The gel clearly shows specificity of amplification. Only full, doubly-ligated LAMPlates support amplification. V1 adapter design seems superior to v2 design. Lane 1, 15 are molecular weight ladders. Lane 2 is SHRK_INS01 inserts-only subjected to solution LAMP amplification reaction. Lane 3, 4 adapter pairs (v1 and v2 respectively) subjected to solution LAMP amplification reaction. Lanes 5,6 are v1-mono-adapted insert subjected to solution LAMP amplification reaction. Lanes 7,8 are v2-mono-adapted insert subjected to solution LAMP amplification reaction. Lanes 9,10 are full, doubly-adapted LAMPlates (v1 and v2 respectively) subjected to solution LAMP amplification reaction. Lanes 11,12 are no-ligase controls for full, doubly-adapted LAMPlates (v1 and v2 respectively) subjected to solution LAMP amplification reaction. Lanes 13, 14 are full, doubly-adapted LAMPlates (v1 and v2 respectively) subjected to solution LAMP amplification reaction using incorrect solution primers (v2 and v1 primers respectively).

Figure 17:
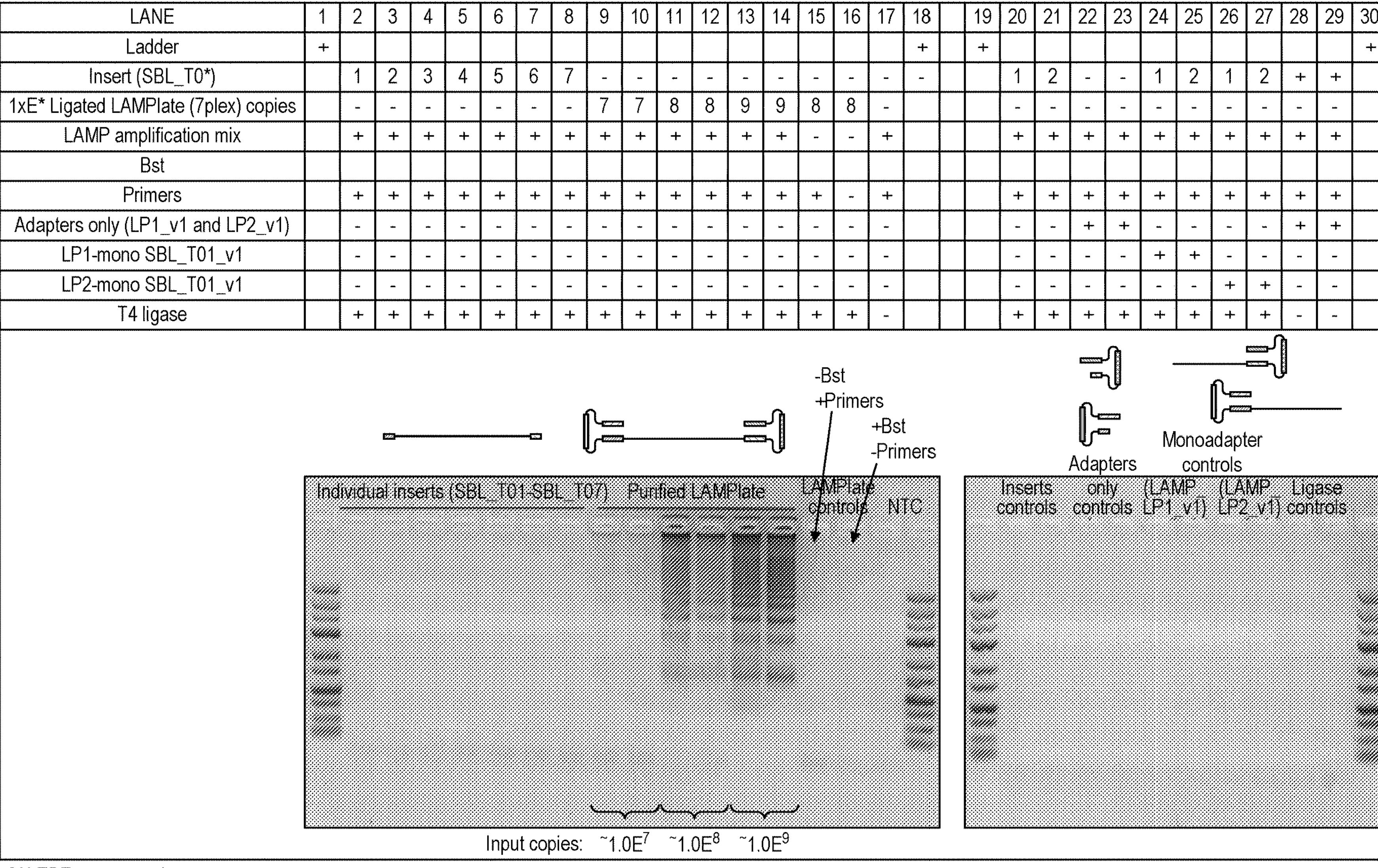

FIG. 17: Solution LAMP amplification of a single LAMPlate prepared by ligation Non-denaturing agarose gel image shows the pattern of bands typical of LAMP amplified DNA with various constructs. The gel clearly shows specificity of amplification. Only full, doubly-ligated LAMPlates support amplification. Lane 1, 18, 19 and 30 are molecular weight ladders. Lane 2-8, 20-21 are ssDNA inserts-only subjected to solution LAMP amplification reaction. Lane 9-16 are a serial dilution of the 7-plex ligation-produced LAMPlate pool (1 E7, 1 E8 and 1 E9 copies input) subjected to solution LAMP amplification reaction. Lanes 22,23 are adapters-only subjected to solution LAMP amplification reaction. Lanes 24, 25 are LP1-monoadapted-insert (insert SBL_T01 and SBL-T02 respectively) subjected to solution LAMP amplification reaction. Lanes 26, 27 are LP2-monoadapted-insert (insert SBL_T01 and SBL-T02 respectively) subjected to solution LAMP amplification reaction. Lanes 28, 29 are no ligase controls (insert SBL_T01 and SBL-T02 respectively) subjected to solution LAMP amplification reaction.

DETAILED DESCRIPTION OF THE EMBODIMENTS

Figure 1:
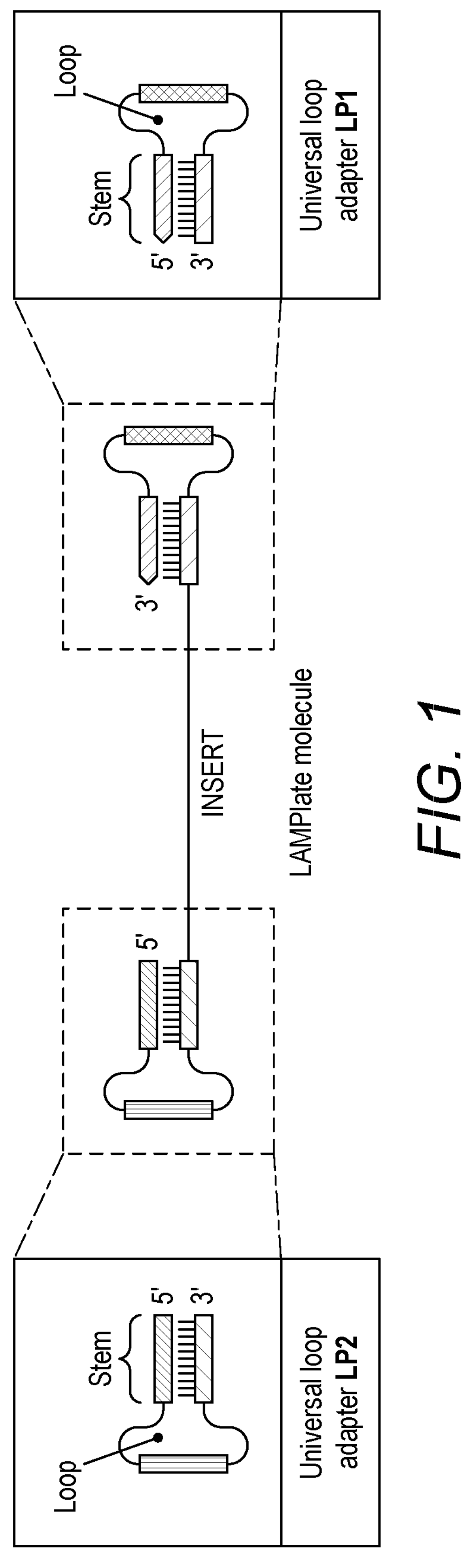
FIG. 1 shows the general LAMPlate structure. The molecule has a single stranded central section flanked by a hairpin at both the 3'- and 5'-ends. The 3' ends can be extended to arrive at the construct shown in FIG. 4. The extension can be the initial phase of the amplification, or can be performed as a separate 'pre-amplification' step.

The addition of hairpin loops (termed LP1 and LP2) to the termini of target template DNA fragments generates a library molecule capable of supporting LAMP amplification, hereby termed a "LAMPlate". The general LAMPlate structure is given in FIG. 1. This pair of hairpin adapters can be the same for all LAMPlate library molecules in a given pool, and so are universal adapters. This feature enables all library molecules in the pool to be interrogated and amplified with a common set of primers specific for these universal hairpin adapters, regardless of the insert sequence. This aspect of the invention provides a route to the in situ amplification of a high multiplex of LAMPlate molecules in a single-pot reaction, something which is difficult or impossible to achieve with standard isothermal LAMP amplification.

The DNA sequence of the universal adapters is platform-specific and can be easily tailored to suit requirements. The only constraints are that the stem region of each adapter needs to be complementary DNA duplex and the loop region needs to connect the two arms of the stem and have a sequence dissimilar to the stem to prevent mis-hybridization. The length and GC content of the stem arms may be critical for efficient formation of the intramolecular hairpin loops and hence the efficiency of the resulting amplification. It is likely that the length of the stem arms is between 15 and 30 bp long and have a Tm in the range of 45-55° C.

The length and GC content of the loop may be critical to achieving efficient hybridization of the amplification primers and hence critical to the efficiency and specificity of the resulting amplification. It is likely that the length of the loop is between 15 and 30 bp long and have a Tm (when annealed to its complementary amplification primer) within the range 55-65° C. There is a requirement for the DNA sequence of LP1 and LP2 hairpin adapters to be sufficiently dissimilar to each other to promote the specificity and efficiency of the resulting LAMPlate amplification. It is anticipated that the pair of adapters will add approximately 90-180 nt of sequence to target inserts.

The stem duplex can be designed to encode for one or more restriction or nicking endonuclease motifs that could be useful in post-amplification processing of the amplified LAMPlate.

There is not anticipated to be a limit to the length of the insert that can be adapted, but for practical purposes, it is likely that inserts of size 50-200 nucleotides will be optimal for LAMPlate amplification efficiency, and that inserts greater than 1000 nucleotides are unlikely to be required.

Figure 2:
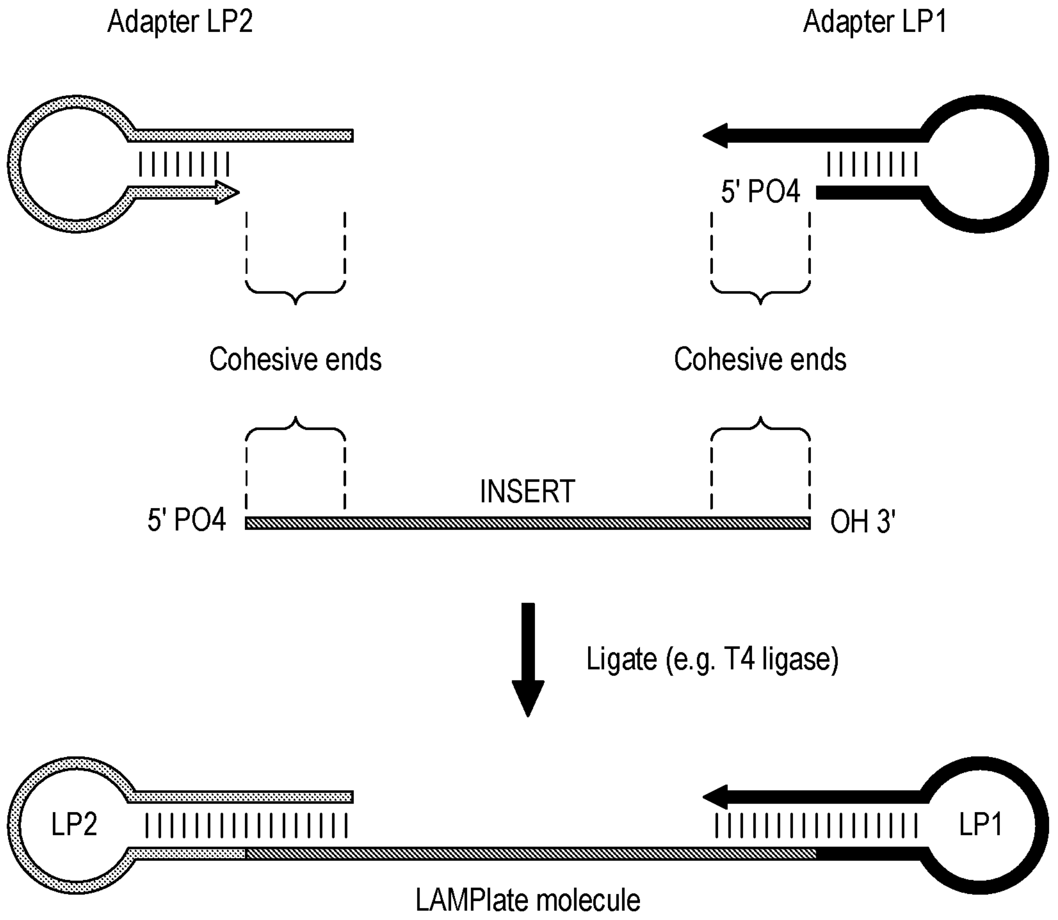
FIG. 2 shows how LAMPlates can be generated simply by the simultaneous ligation of LP1 and LP2 adapters to a single stranded template molecule.
Figure 3:
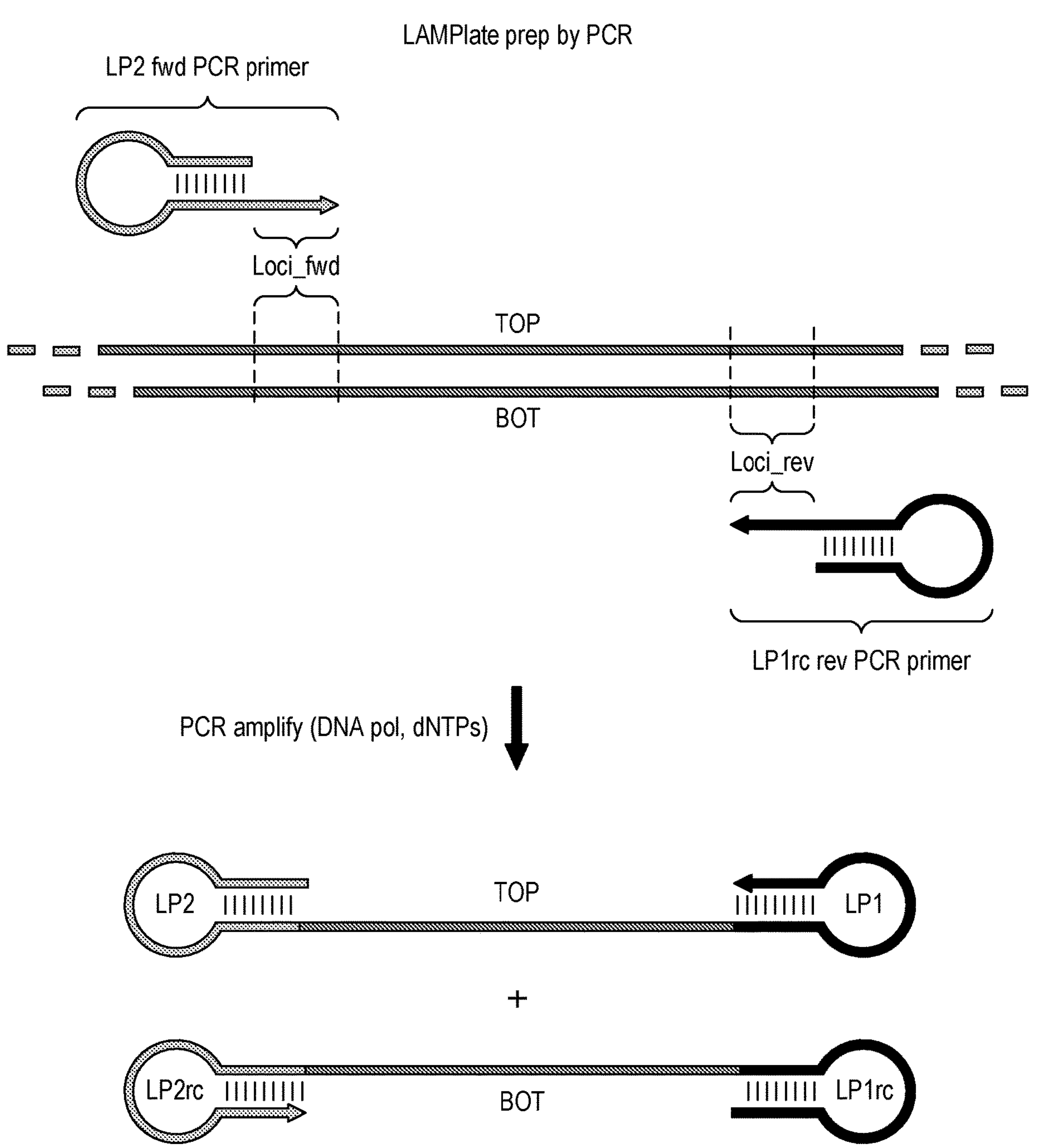
FIG. 3 shows how LAMPlates can be generated via PCR by using loci-specific PCR primers with 5' stem-loop structures.

LAMPlates can be generated simply by the simultaneous ligation of LP1 and LP2 adapters to a single stranded template molecule (FIG. 2), or via PCR by using loci-specific PCR primers with 5' stem-loop structures (FIG. 3).

The templates are suitable for amplification, which forms concatamers. Amplification is performed using a strand displacing polymerase. The hairpin stems are self-complementary such that when displaced by the polymerase to become single stranded, the released single stranded 3'-ends can self-anneal and extend. Thus amplification can be performed effectively using the copied molecule as its own template.

Disclosed is a population of single stranded nucleic acid molecules (ss1) of at least 50 nucleotides in length wherein the single strands have a different sequence and each of the single strands has a common hairpin region at the 3' end (LP1) and a common hairpin region at the 5' end (LP2), wherein each hairpin has hybridising stem arms of between 15-30 base pairs in length, the stem arms having a Tm in the range of 45-55° C.

The source single stranded nucleic acid may be a genomic polynucleotide. The source material may be eukaryotic, prokaryotic, or archaeal. One or more source materials may be provided. The source nucleic acid may represent a fragment of a genome; for example, a single chromosome, or a single genomic locus (for example, for rapid sequencing of allelic polymorphisms). In particular examples the amplification may be specific for pathogenic material within a sample. For example the amplification may select bacterial or viral nucleic acids present within a human sample. Templates may be DNA, RNA, or the cDNA copies thereof.

The viral nucleic acids may originate from a coronavirus. The coronaviruses are a group of related RNA viruses that cause disease in mammals and birds. They cause respiratory tract infections such as the common cold, severe acute respiratory syndrome (SARS), Middle East respiratory syndrome (MERS) and severe acute respiratory syndrome coronavirus 2 (SARS-CoV-2) also known as COVID-19.

SARS-CoV-2 is the strain of coronavirus responsible for the COVID-19 global pandemic, it is a positive-sense single-stranded RNA virus. Each SARS-CoV-2 virus is 50-200 nanometres in diameter, with four structural proteins, known as the spike (S), envelope (E), membrane (M) and nucleocapsid (N) proteins. The N protein holds the RNA genome, and the S, E, and M proteins together create the viral envelope.

Thus, in one embodiment, the amplification may select for one or more viral nucleic acids which encode the each of the structural proteins of SARS-CoV-2.

In one embodiment, the amplification may select for one or more nucleic acids, the presence of which indicates an active SARS-CoV-2 infection in a host. In one embodiment, the amplification may select for one or more nucleic acids, the presence of which indicates a previous SARS-CoV-2 infection in a host. These nucleic acids may be nucleic acids produced by a host as part of an immune response to the SARS-CoV-2 infection.

In one embodiment, each single stranded nucleic acid molecule (ss1) has a single stranded loop (L) between the stem arms, the loop being 15-30 nucleotides in length and having a Tm in the range of 55-65° C. when annealed to a complementary primer.

In one embodiment, the single stranded nucleic acid molecules are 50-200 nucleotides in length. In one embodiment, the single stranded nucleic acid molecules are 100-200 nucleotides in length.

In one embodiment, the single stranded nucleic acid molecules of the population are between 190 to 380 in total length and the 3'- and 5' ends have 15-30 base pairs of double stranded sequence at a temperature of below 45° C.

Disclosed is a method for the concatameric amplification of a plurality of nucleic acid sequences comprising taking a population of nucleic acid molecules according to any one of the previous embodiments of the invention and a reaction mixture containing a strand displacing polymerase, nucleotide monomers and amplification primers wherein at least one of the amplification primers (P1') is complementary to at least a portion of the loop (L) of LP1 and one of the amplification primers (P2) contains the same sequence as at least a portion of a copy of the loop of LP2 (LP2').

Disclosed is a method for the concatameric amplification of a plurality of nucleic acid sequences comprising, a) taking a population of different single stranded nucleic acid molecules (ss1) of at least 50 nucleotides in length wherein the single strands have a different sequence and each of the single strands has a common hairpin region at the 3' end (LP1) and a common hairpin region at the 5' end (LP2), wherein each hairpin has hybridising stem arms of between 15-30 base pairs in length, the stem arms having a Tm in the range of 45-55° C.; and b) amplifying the population of different single stranded nucleic acid molecules (ss1) using a reaction mixture containing a strand displacing polymerase, nucleotide monomers and amplification primers wherein at least one of the amplification primers (P1') is complementary to at least a portion of the loop (L) of LP1 and one of the amplification primers (P2) contains the same sequence as at least a portion of a copy of the loop of LP2 (LP2').

In one embodiment of the method, the 3' end of the stem arm is extended to make a complete copy of the single stranded nucleic acid molecules of at least 50 nucleotides in length (ss1') and a complete copy of sequence LP2 (termed LP2'). The extension can be the initial part of the amplification reaction. Alternatively the 3' end of the stem arm can be extended to make a complete copy of the single stranded nucleic acid molecules of at least 50 nucleotides in length (ss1') and a complete copy of sequence LP2 (termed LP2' prior to then placing the extended molecule in the amplification reaction mixture.

In a further embodiment of the method, P1' hybridises to the loop of LP1 and extends to strand displace and thereby separate LP2 and LP2'. The strand displacement produces a complementary copy of ss' and LP2' (i.e. a replica of ss and a replica of LP2).

In a further embodiment of the method, the stem arms of the end of LP2' can self-prime to extend and make a complete copy of all of ss1', LP1, ss1 and LP2.

In a further embodiment of the method, the amplification primer P2 hybridises to the loop of LP2' and extends to displace all of ss1', LP1, ss1 and LP2.

In a further embodiment of the method, the released end LP2' can repeatedly self-prime to copy the concatamer ss1', LP1 and ss1.

In a further embodiment of the method, the amplification primer P1 is attached to a solid support.

In a further embodiment of the method, the amplification primer P2 is in solution.

It is envisioned that the amplification method can be used to generate surface-bound amplification products, and specifically clonal-surface-bound amplification products according to the scheme shown in FIGS. 7 to 12.

A DNA oligo primer whose sequence is complementary to the LP1 loop of the LAMPlate, termed LP1 RC, is immobilized to a solid support (e.g. surface of a slide, chip or bead). This functionalised surface can be incubated in the presence of a solution comprising a dilute concentration of LAMPlate (e.g. 1-1000 pM) in a suitable hybridization buffer at a specified temperature for a specified time. This allows the LAMPlate to anneal to the immobilized primer through sequence complementarity with the single-stranded LAMPlate LP1 loop region. This process can be referred to as "LAMPlate seeding".

Once seeded, excess LAMPlate can be washed off leaving only surface-primer hybridized molecules in situ. Adding a strand displacing DNA polymerase (e.g. Bst 2.0 WarmStart® DNA Polymerase or Phi29 polymerase) and dNTPs in an appropriate reaction buffer will allow extension from the free-3' termini of the LAMPlate and simultaneously from the free-3' termini of the surface primer hybridized to LAMPlate loop LP1. This surface primer extension causes displacement of the extended LAMPlate duplex strand, thus forming a molecule which is partly single stranded and partly double stranded, immobilised via the 5' end of the shorter strand.

The extended 3' end of the LAMPlate is therefore single stranded and able to self-prime. The self-primed end can extend to make a complete copy, and in the process displacing itself from the immobilised strand. The material thereby displaced into bulk solution is fully self-complementary apart from a single loop, that loop being of a different sequence to the loop which hybridises to the surface, and therefore the material in bulk solution plays no further part in the amplification.

This displacement causes the spontaneous re-formation of the intramolecular LP2' loop at the 3'-terminus of the immobilized copy which can self-prime and extends to generate a surface-bound duplex with a LP2' hairpin distal to the surface. Thus the immobilised material is mostly double stranded, apart from one internal loop LP2'.

Optionally the fluidic reagents can be changed at this point in order to remove the displaced material, thereby preventing any further amplification of this material, which may contaminate the amplification process or simply consume the amplification reagents.

The amplification on the surface requires a non-immobilised primer complementary to the immobilised single stranded loop (i.e. a primer which hybridises to LP2'). The solution oligo primer, termed LP2, complementary to the LP2' loop of the immobilized duplex product can anneal to the LP2' loop and extend. This LP2-primer extension makes a faithful copy of half of the immobilized duplex and simultaneously displaces the 3' end of the strand complementary to the copied strand. The displaced 3' end spontaneously re-forms the LP1 intramolecular hairpin which is both able to self-prime and hybridise to a further copy of immobilised primer LP1 RC via the single stranded loop. Thus two new extendable 3' ends are available.

The process of the bridging of one strand from one copy to an adjacent surface primer, thereby forming a new propagated interaction is termed "template walking". Subsequent and simultaneous double extension from the free-3' ends of the hybridized LP1 loop and from the free-3' end of the newly formed duplex between the LP1 loop of the walked template strand and the second LP1 RC surface primer enables the generation of a two surface-immobilized hairpin duplexes via extension, strand displacement and a self-primed complementary extension. The first duplex being a double concatamer of the initial LAMPlate with a LP1 loop distal to the surface (i.e. four contiguous double stranded sets of ss and ss'), and the second being a duplex with hairpin loop LP1 distal from the surface and a single concatamer (i.e. two repeats of ss and ss') (shown in FIG. 12).

Both immobilised duplexes now have single stranded loops which are complementary to the LP1 RC surface primer. The surface primer can therefore hybridise to the centre of the immobilised strand. Extension displaces the immobilised 3' end having loop LP1. The re-formation of LP1 gives a self-primer end and a loop which can be immobilised to a further copy of primer LP1 RC. This forms two new extendable 3' ends, one self-primed and one on the immobilised primer. The amplification is therefore self-sustaining via cycles of hybridisation with the support causing displacement and self-primed extension.

This continuous process of primer hybridization, extension, displacement and template walking continues for the duration of the amplification reaction or until the reagents in the reaction are consumed, whichever happens first. The product of these amplification and template-walking cycles is the generation of multiple, faithful surface-bound copies of the original seeded LAMPlate, as intramolecular concatemeric repetitive duplexes in close spatial proximity to the original seeded LAMPlate. A plurality of such close proximity faithful duplex copies can be referred to as clone, or a cluster or a colony and as such the original single stranded portion of the seeded LAMPlate can be said to have been "clonally amplified".

Also disclosed is a method wherein the presence, absence or sequence of the nucleic acid amplification product of the invention is determined.

Also disclosed is a device for the amplification of a plurality of nucleic acid sequences, comprising a solid support with immobilised amplification primers which are hybridised to a population of nucleic acid molecules described herein.

A kit for the amplification of a plurality of nucleic acid sequences is also disclosed, comprising:

a. a first hairpin adaptor having hybridising stem arms of between 15-30 base pairs in length, the stem arms having a Tm in the range of 45-55° C. and a single stranded loop (L) between the stem arms, the loop being 15-30 nucleotides in length and having a Tm in the range of 55-65° C. when annealed to a complementary primer;

b. a second hairpin adaptor having hybridising stem arms of between 15-30 base pairs in length, the stem arms having a Tm in the range of 45-55° C. and a single stranded loop (L) between the stem arms, the loop being 15-30 nucleotides in length and having a Tm in the range of 55-65° C. when annealed to a complementary primer;

c. a solid support with amplification primers immobilised wherein the primers are complementary to at least a portion of Loop L of the first hairpin adaptor; and d. a nucleic acid polymerase and nucleoside triphosphates.

Methods

Preparation of LAMPlates by Ligation (A69_SBLAMP_E001)

Materials

LP1 oligo (LAMP_LP1_v1)

LP2 oligo (LAMP_LP2_v1)

Template oligo (INS01)

T4 DNA ligase 2000 U/uL (NEB, M0202T)

Zymo Oligo Clean & Concentrator® purification columns

EB buffer (10 mM Tris.HCl pH 8.0)

Oligo sequences

| Oligo name | Sequence (5'-3') |
|---|---|
| LAMP_LP1_v1 (SEQ ID NO: 1) | PO4-TCCAGTTATCTCGTATGCCGTCTTCTGCTTGAACTGGATCTATAAG |
| LAMP_LP2_v1 (SEQ ID NO: 2) | GACTCCTCAGCTAGCGAATGATACGGCGACCACCGACGCTAGCT |
| LAMP_LP1_v2 (SEQ ID NO: 3) | PO4-TCCAGTTTTCAGAGGATCTAGTCGGCAACTGGATCTATAAG |
| LAMP_LP2_v2 (SEQ ID NO: 4) | GACTCCTCAGCTAGCGCTTGGCTTCATTGTGGTCCGCTAGCT |
| SHRK_INS01 (SEQ ID NO: 5) | PO4-GAGGAGTCGCTCCATCGGTGTGTACGCGATGGATACCGGCT CAGGCGCAACTTATAGA |

Method

Typically, ligation reactions were prepared by mixing LP1 and LP2 adapter oligos in equimolar ratios (280 pmol each adapter) with template oligo INS01 (130 µmol) in 1× ligation buffer. Reactions were mixed briefly by vortexing. The resulting oligos were heat denatured at 95° C. for 3 minutes and then annealed by a slow cooling ramp on a thermocycler (to 15° C. at −0.1° C./sec). The ligation reaction was initiated by the addition of 2000 U T4 DNA ligase (1 uL of 2000 U/uL T4 ligase stock), vortexed briefly to mix and then incubated at 15° C. for 30 minutes. The ligase was inactivated by heat-kill at 75° C. for 5 minutes and purified using Zymo Oligo Clean & Concentrator® spin columns. Final elution was in EB buffer. Samples were run down a 3% TBE agarose gel stained with gel red stain for visualization.

FIG. 13 Legend

Non-denaturing agarose gel image shows the INS01 LAMPLate ligation products, the trend in molecular weight shift from adapters-only, monoadapted-INS01 and doubly-adapted-INS01 are clearly observable. Lane 1 and 13 are molecular weight ladders. Lane 2 is insert only. Lane 3-6 are adapter pairs LP1 and LP2 for two designs (v1 and v2) and two concentrations (either 280 pmol L3,4 or 660 pmol L5, 6 per adapter). Lane 7-10 are monoadapter ligations. Lane 11-12 are full ligations for v1 and v2 adapter designs.

Preparation of LAMPlates by Looped-PCR (A69_SBLAMP_E022)

Materials

- Looped PCR_F primers
- Looped PCR_R primers
- Template genomic DNA (bacteriophage PhiX-174, NEB, N3022L)
- PCR buffer (5× Buffer component, Thermo F(22S)
- Phire® II HS DNA polymerase (Polymerase component, Thermo F422S)
- 10 mM dNTP mix
- QIAquick® PCR purification columns
- EB buffer (10 mM Tris.HCl pH 8.0)

Oligos

| Amplicon_ref | Oligo_name | F/R primer | Sequence | PhiX_coord (length) |
|---|---|---|---|---|
| LAMP_PhiX_01 | SBL_PHIX_01 (SEQ ID NO: 6) | F | G*A*C*TCCTCAGCTAGCGAATGATACGGCGACCACCGACGCTAGCTGAGGAGTCCAATCCGTACGTTTCCAGAC | 413-640 (228 bp) |
| | SBL_PHIX_02 (SEQ ID NO: 7) | R | CTTATAGATCCAGTTCAAGCAGAAGACGGCATACGAGATAACTGGATCTATAAGACGGCAGCAATAAACTCAAC | |
| LAMP_PhiX_02 | SBL_PHIX_03 (SEQ ID NO: 8) | F | G*A*C*TCCTCAGCTAGCGAATGATACGGCGACCACCGACGCTAGCTGAGGAGTCTTAAAGCCGCTGAATTGTTC | 743-930 (188 bp) |
| | SBL_PHIX_04 (SEQ ID NO: 9) | R | CTTATAGATCCAGTTCAAGCAGAAGACGGCATACGAGATAACTGGATCTATAAGTGCCTTTAGTACCTCGCAAC | |
| LAMP_PhiX_03 | SBL_PHIX_05 (SEQ ID NO: 10) | F | G*A*C*TCCTCAGCTAGCGAATGATACGGCGACCACCGACGCTAGCTGAGGAGTCCGCCTACTGCGACTAAAGAG | 1904-2089 (186 bp) |
| | SBL_PHIX_06 (SEQ ID NO: 11) | R | CTTATAGATCCAGTTCAAGCAGAAGACGGCATACGAGATAACTGGATCTATAAGAACGATACCACTGACTGACCCTCA | |
| LAMP_PhiX_04 | SBL_PHIX_07 (SEQ ID NO: 12) | F | G*A*C*TCCTCAGCTAGCGAATGATACGGCGACCACCGACGCTAGCTGAGGAGTCCTTCTTCGGCACCTGTTTTA | 2506-2694 (189 bp) |
| | SBL_PHIX_08 (SEQ ID NO: 13) | R | CTTATAGATCCAGTTCAAGCAGAAGACGGCATACGAGATAACTGGATCTATAAGAAAAATTTAGGGTCGGCATC | |
| LAMP_PhiX_05 | SBL_PHIX_09 (SEQ ID NO: 14) | F | G*A*C*TCCTCAGCTAGCGAATGATACGGCGACCACCGACGCTAGCTGAGGAGTCTCAAGGTGATGTGCTTGCTA | 3072-3293 (222 bp) |
| | SBL_PHIX_10 (SEQ ID NO: 15) | R | CTTATAGATCCAGTTCAAGCAGAAGACGGCATACGAGATAACTGGATCTATAAGCCAAGTCCAACCAAATCAAG | |

Method

Individual PCR amplification reactions were prepared for each PhiX amplicon using pairs of SBL_PHIX PCR primers. Each 50 uL PCR reaction consisted of 10 ng PhiX-174 genomic DNA, 20 pmol each of PCR_F and PCR_R primer, 10 nmol of dNTP mix, 1 μL of Phire® II HS DNA polymerase in 1× Phire® PCR buffer. Reaction mixes were denatured at 98° C. for 2 minutes and then subjected to 25 subsequent cycles of denaturation (95° C. for 30 s), annealing (60° C. for 20 s) and extension (72° C. for 20 s). Amplicons were purified using QIAquick® PCR clean-up columns and final elutions were in EB buffer. Samples were run down a 3% TBE agarose gel stained with gel red stain for visualization.

FIG. 14 Legend

Non-denaturing agarose gel image shows the 5 individual loci-specific PhiX-174 PCR amplicons using looped-PCR primers, clean bands show the amplification of products of the expected molecular weight. Lane 1 and 7 are molecular weight ladders. Lane 2-6 are amplicons for regions LAMP-_PhiX_01-05. The 5' loops of the PCR_F and PCR_R primers add an additional 103 nt onto the insert length hence the expected shift in molecular weight over the anticipated amplicon insert length.

Solution LAMP Amplification Using Full-Length Ultramer LAMPlate Oligo Materials

LAMPlate ultramer template oligo (LAMP_T01_v1)
Solution LAMP amplification primers (LP1rc_v1 and LP2_v1)
Warm start LAMP amplification kit (NEB, E1700S)
Zymo Oligo Clean & Concentrator® purification columns
EB buffer (10 mM Tris.HCl pH 8.0)

| Oligos | |
|---|---|
| Oligo name | Sequence (5'-3') |
| LAMP_T01_v1 (SEQ ID NO: 16) | GACTCCTCAGCTAGCGAATGATACGGCGACCACCGACGCTAGCTG AGGAGTCGCTCCATCGGTGTGTACGCGATGGATACCGGCTCAGGC GCAACTTATAGATCCAGTTATCTCGTATGCCGTCTTCTGCTTGAACT GGATCTATAAG |
| LP1rc_INV_v1 (SEQ ID NO: 17) | CTTATAGATCCAGTTCAAGCAGAAGACGGCATAC*G*A*G |
| LP2_INV_v1 (SEQ ID NO: 18) | GACTCCTCAGCTAGCGAATGATACGGCGAC*C*A*C |

Method

Example 25 uL solution LAMP amplification reactions were prepared by diluting 12.5 uL of 2× LAMP mastermix (containing buffer, Bst 2.0 WarmStart® DNA Polymerase and dNTPs) with ultramer LAMPlate LAMP_T01_v1 (0.25-2.5 fmol), LAMP primers LP1_rc_INV_v1 (230 μmol) and LP2_INV_v1 (230 μmol) and MilliQ water. Reactions were initiated by warming to 65° C. and incubating reactions for 60 minutes. Reactions were either stopped by the addition of 3 uL 500 mM EDTA or purified directly by QIAquick® PCR clean-up columns. Samples were run down a 3% TBE agarose gel stained with gel red stain for visualization.

FIG. 15 Legend

Non-denaturing agarose gel image shows the pattern of bands typical of LAMP amplified DNA. The ladder of bands of increasing molecular weight is consistent with the tandem repeat concatemer amplification indicative of the method. Lane 1 and 6 are molecular weight ladders. Lane 2-3 and 4-5 are LAMPlicons generated by the solution LAMP amplification of a full length ultramer LAMPlate LAMP_T01_v1 at 1 E8 and 1 E10 copies respectively.

Solution LAMP Amplification Using a Single Ligation-Prepared LAMPlate

Materials

Purified ligation-prepared LAMPlate (SHRK_INS01)
LAMP adapters (LP1_v1, LP2_v1, LP1_v2 and LP2_v2)
Solution LAMP amplification primers (LP1_rc_v1, LP2_v1 LP1_rc_v2 and LP2_v2)
Warm start LAMP amplification kit (NEB, E1700)
Zymo Oligo Clean & Concentrator® purification columns
EB buffer (10 mM Tris.HCl pH 8.0)

| Oligos | |
|---|---|
| Oligo name | Sequence (5'-3') |
| LAMP_LP1_v1 (SEQ ID NO: 1) | PO4- TCCAGTTATCTCGTATGCCGTCTTCTGCTTGAACTGGATCTATAAG |

-continued

| Oligos | |
|---|---|
| Oligo name | Sequence (5'-3') |
| LAMP_LP2_v1 (SEQ ID NO: 2) | GACTCCTCAGCTAGCGAATGATACGGCGACCACCGACGCTAGCT |
| LAMP_LP1_v2 (SEQ ID NO: 3) | PO4-TCCAGTTTTCAGAGGATCTAGTCGGCAACTGGATCTATAAG |
| LAMP_LP2_v2 (SEQ ID NO: 4) | GACTCCTCAGCTAGCGCTTGGCTTCATTGTGGTCCGCTAGCT |
| SHRK_INS01 (SEQ ID NO: 5) | PO4-GAGGAGTCGCTCCATCGGTGTGTACGCGATGGATACCGGCT CAGGCGCAACTTATAGA |
| LP1rc_INV_v1 (SEQ ID NO: 17) | CTTATAGATCCAGTTCAAGCAGAAGACGGCATAC*G*A*G |
| LP2_INV_v1 (SEQ ID NO: 18) | GACTCCTCAGCTAGCGAATGATACGGCGAC*C*A*C |
| LP1rc_INV_v2 (SEQ ID NO: 19) | 5' CTTATAGATCCAGTTGCCGACTAGATCCT*C*T*G |
| LP2_INV_v2 (SEQ ID NO: 20) | 5' GACTCCTCAGCTAGCGCTTGGCTTCATTG*T*G*G |

Method

Figure 4:
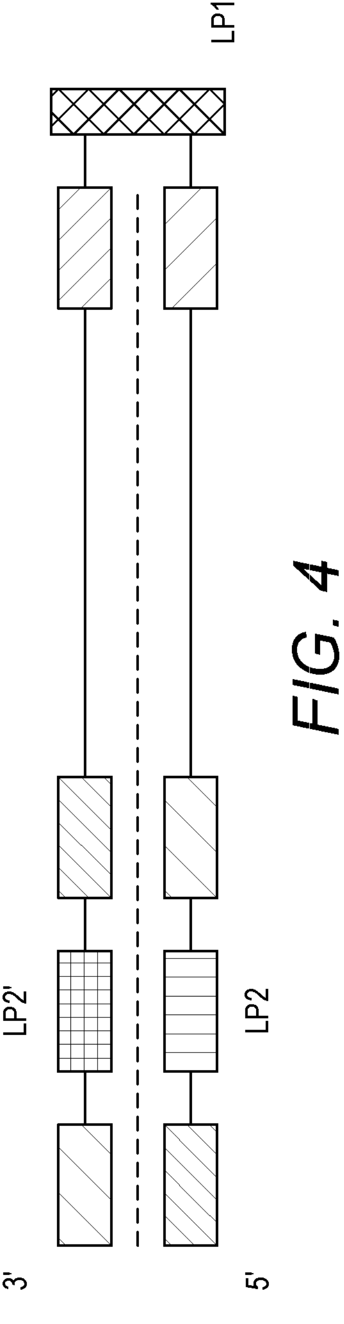
FIG. 4 shows the LAMPlates following an intra-molecular self-primed extension from the internal 3' end. The extension opens the hairpin via strand displacement to reach the 5' end of the sequence without requiring any further primers. The extension can be the initial phase of the amplification, such that amplification is initiated using the construct of FIG. 1, or can be performed as a separate 'pre-amplification' step, in which case the material being amplified is shown as in FIG. 4.
Figure 5:
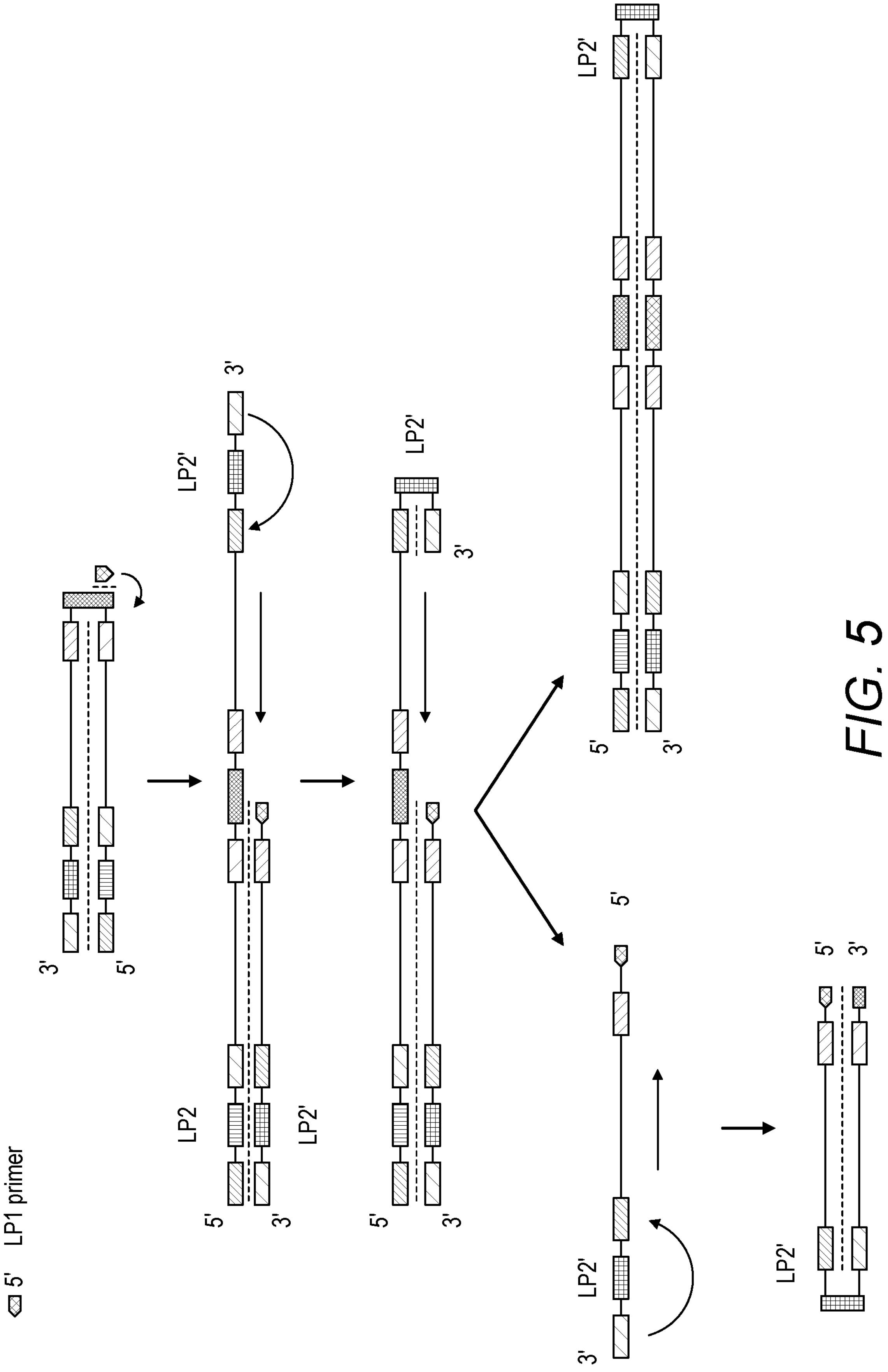
FIG. 5 shows extension from a first primer hybridised to the internal single stranded loop (primer LP1, hybridising to LP1). Following extension the molecule is half single stranded and half double stranded. The displaced 3'-end has a hairpin stem that can self-prime (LP2'), thereby making a concatamer and displacing the extended primer. The displaced extended primer also has a self-complementary end that can self-prime, also LP2'. Thus the first primer gives rise to a 'single' copy and a double copy of the double stranded template, each having a blunt end and a closed loop end (LP2'). Both central loops are single stranded regions of the same sequence.
Figure 6:
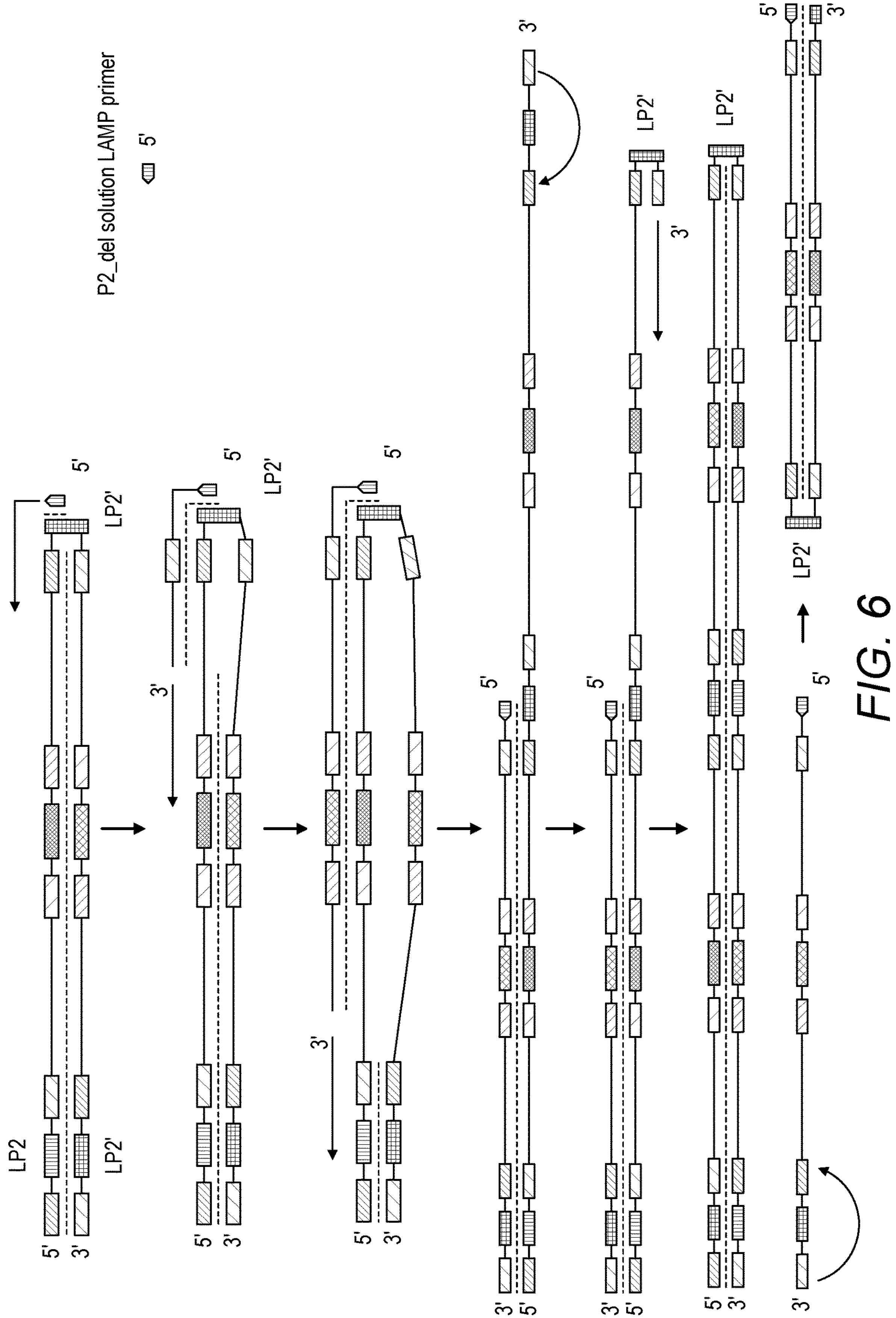
FIG. 6 shows extension from a second primer hybridised to the newly formed internal single stranded loop (primer P2, hybridising to LP2'. Following primer extension the molecule is again half single stranded and half double stranded. The displaced 3'-end has a hairpin stem that can self-prime (again LP2'), thereby making a concatamer and displacing the extended primer. The displaced extended primer also has a self-complementary end that can self-prime. Thus the first primer gives rise to a 'single' copy and a double copy of the double stranded template, each having a blunt end and a closed loop end (LP2'). Both central loops are single stranded regions of the same sequence (LP2'), the loops having the same sequence as the loops from the first stage of amplification. The P2 primer can repeatedly hybridise and extend, thereby making multiple copies of increasing length.
Figure 7:
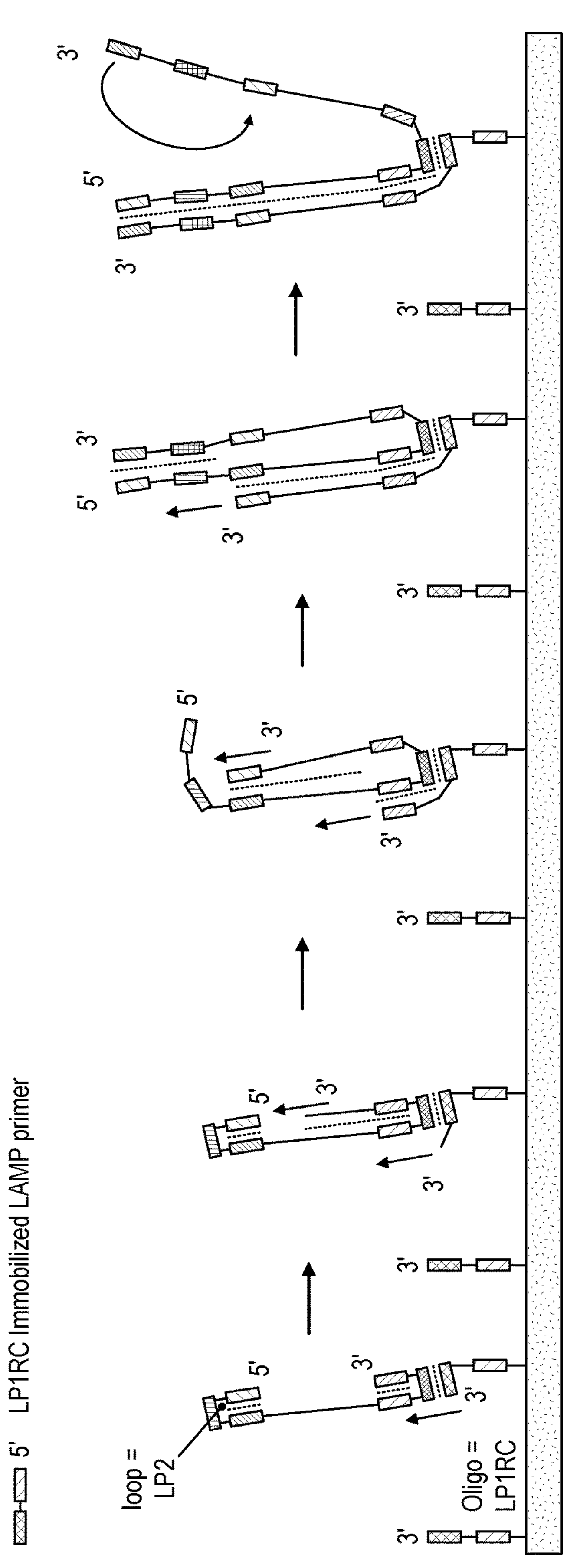
FIG. 7 shows the equivalent to FIG. 4, only with the amplification primer LP1 immobilised. The self-primed 3' end of the LAMPlate and the 3' end of the immobilised primer can both undergo extension. The extended material takes the form of a double stranded section and a single stranded section (FIG. 7).
Figure 8:
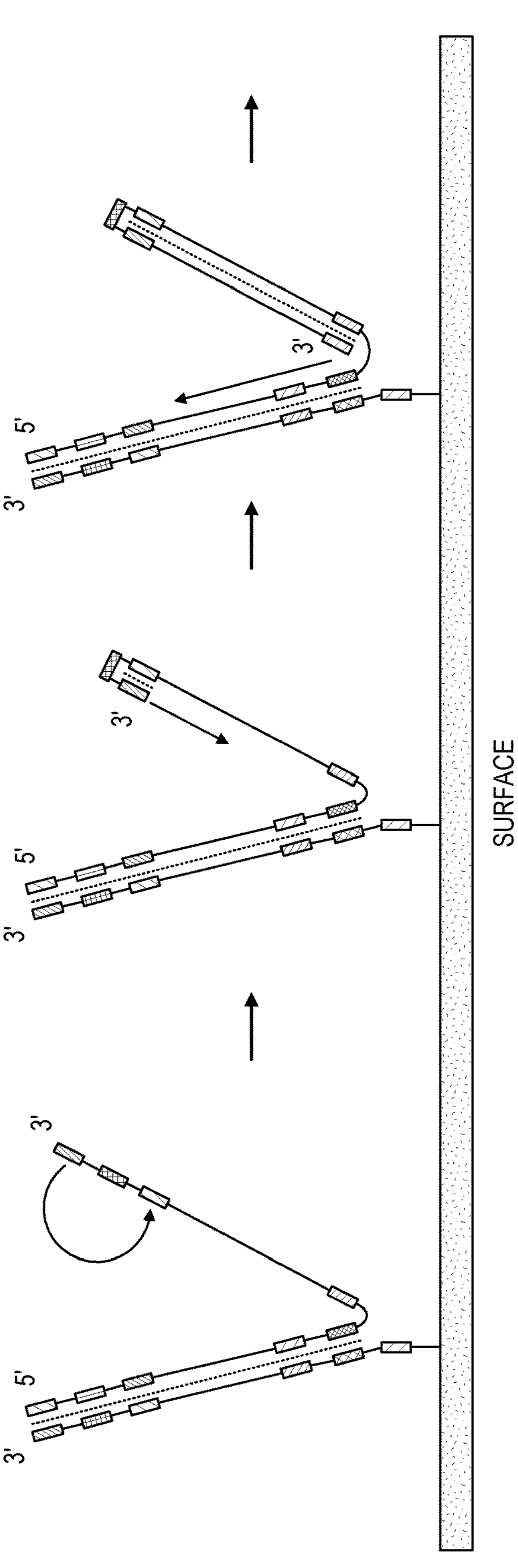
FIG. 8 shows the single stranded section has a self-priming 3'-end that can undergo extension and thereby removes itself from the solid support into solution.
Figure 9:
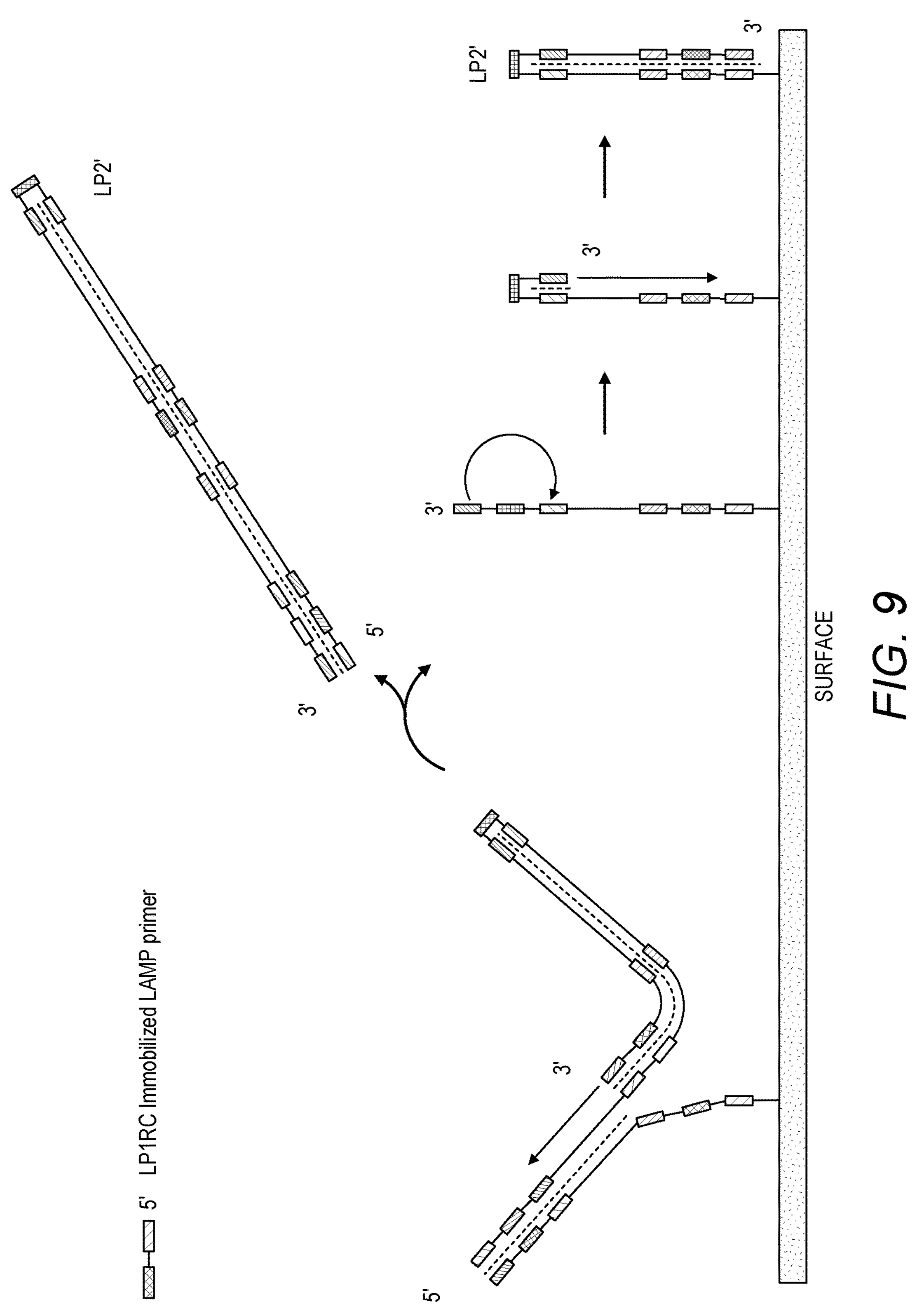
FIG. 9 shows the displaced material is 'dead' and no complementary primers are on the support; however the displacement releases the 3' end of the immobilised product, which can self-prime and extend to make the immobilised material fully double stranded apart from the central loop.
Figure 10:
FIG. 10 shows displacement using a solution phase primer hybridised to the immobilised loop. A primer hybridised to the loop can extend, thereby displacing the 3' end of the immobilised molecule. The displaced 3' end can self-prime and thereby extend. However the displaced 3' end also releases a free single stranded loop that is complementary to the immobilised primer. The loop can hybridise to a localised primer and thereby extend a localised copy of itself.
Figure 10:
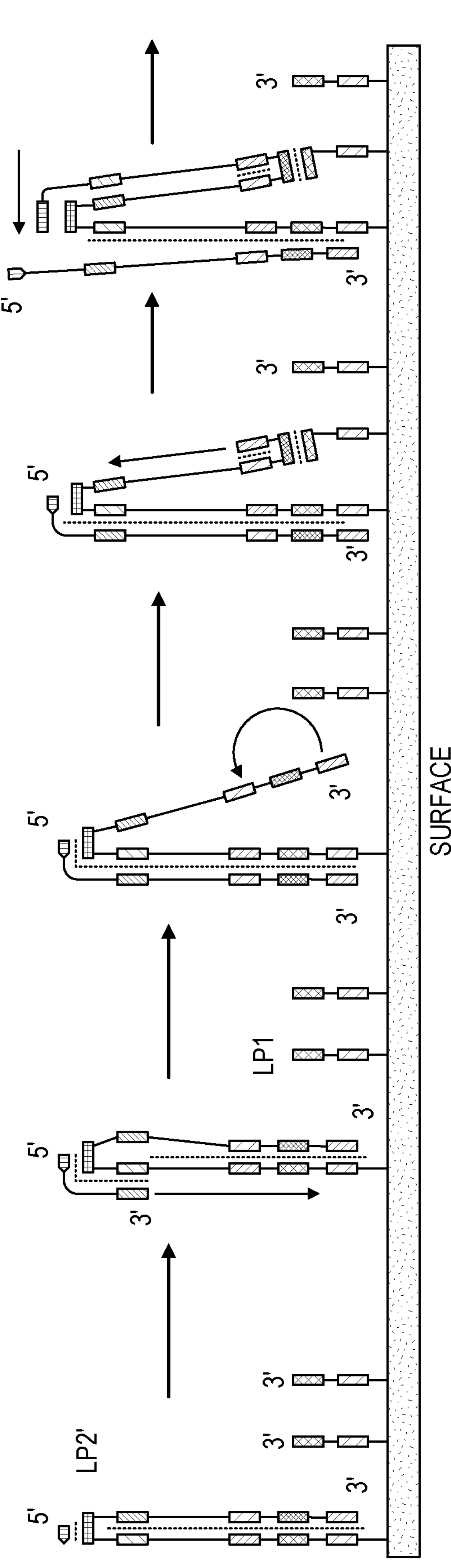
Figure 11:
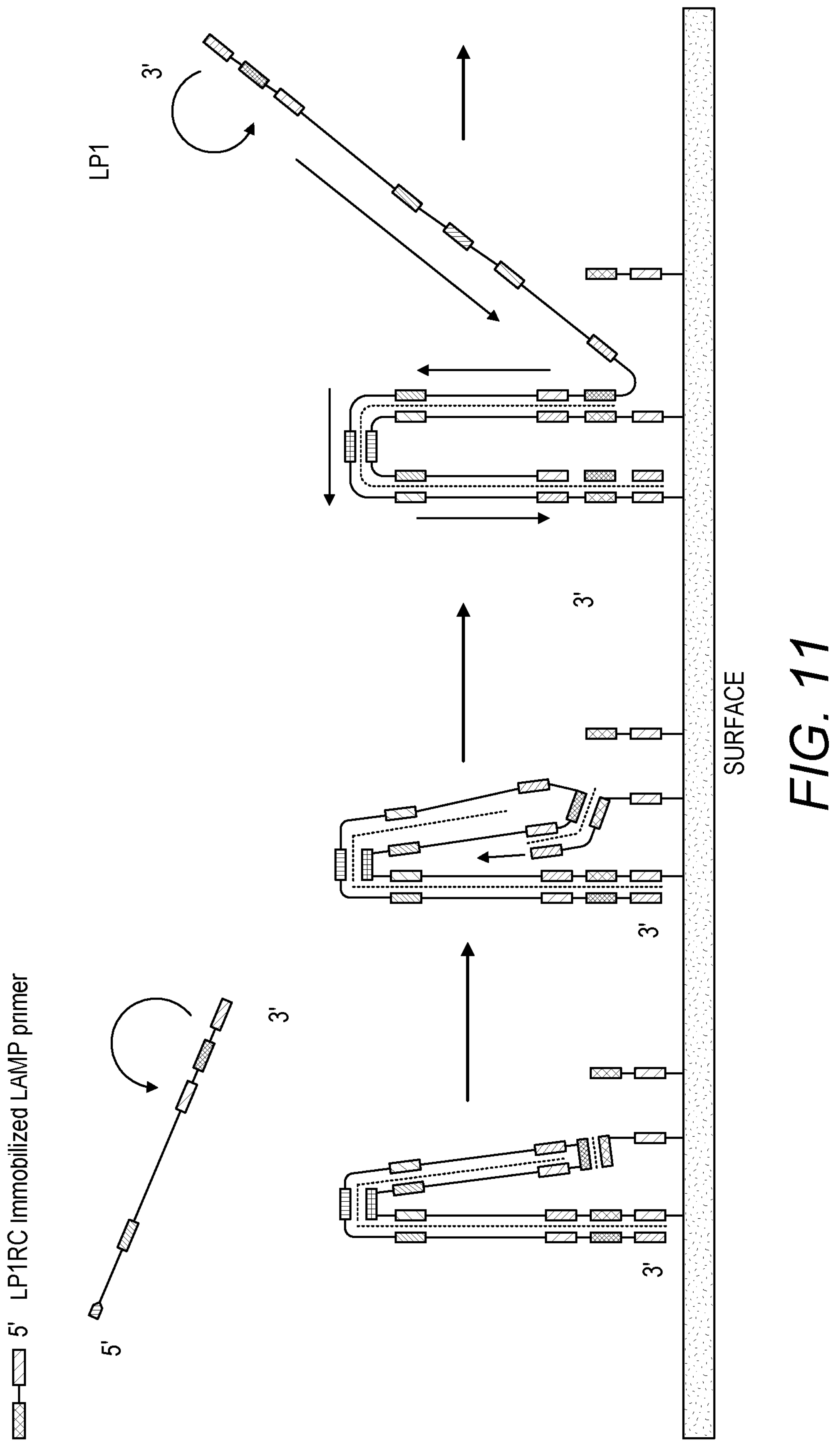
In FIG. 11, akin to the single and double loops in solution, each amplicon on the surface now has a single and double loop localised within the reach of the length of the immobilised nucleic acid.
Figure 12:
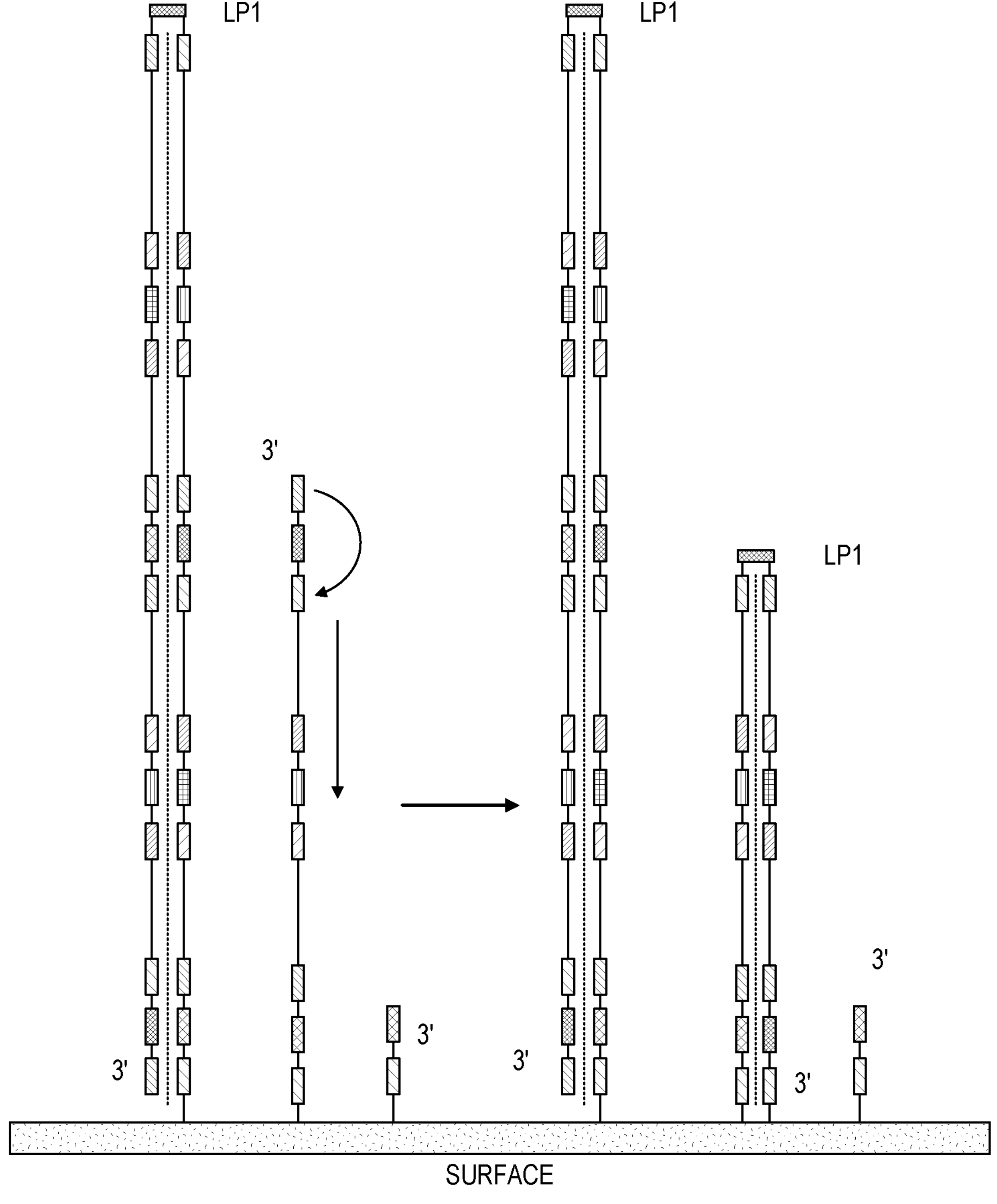
In FIG. 12, the extended product from the non-immobilised primer can form a double stranded molecule in solution. The immobilised primers LP1 can hybridise to the loops, thereby enabling further amplification spatially localised within the reach of the immobilised template. Thus the strands can be locally amplified.
Figure 13:
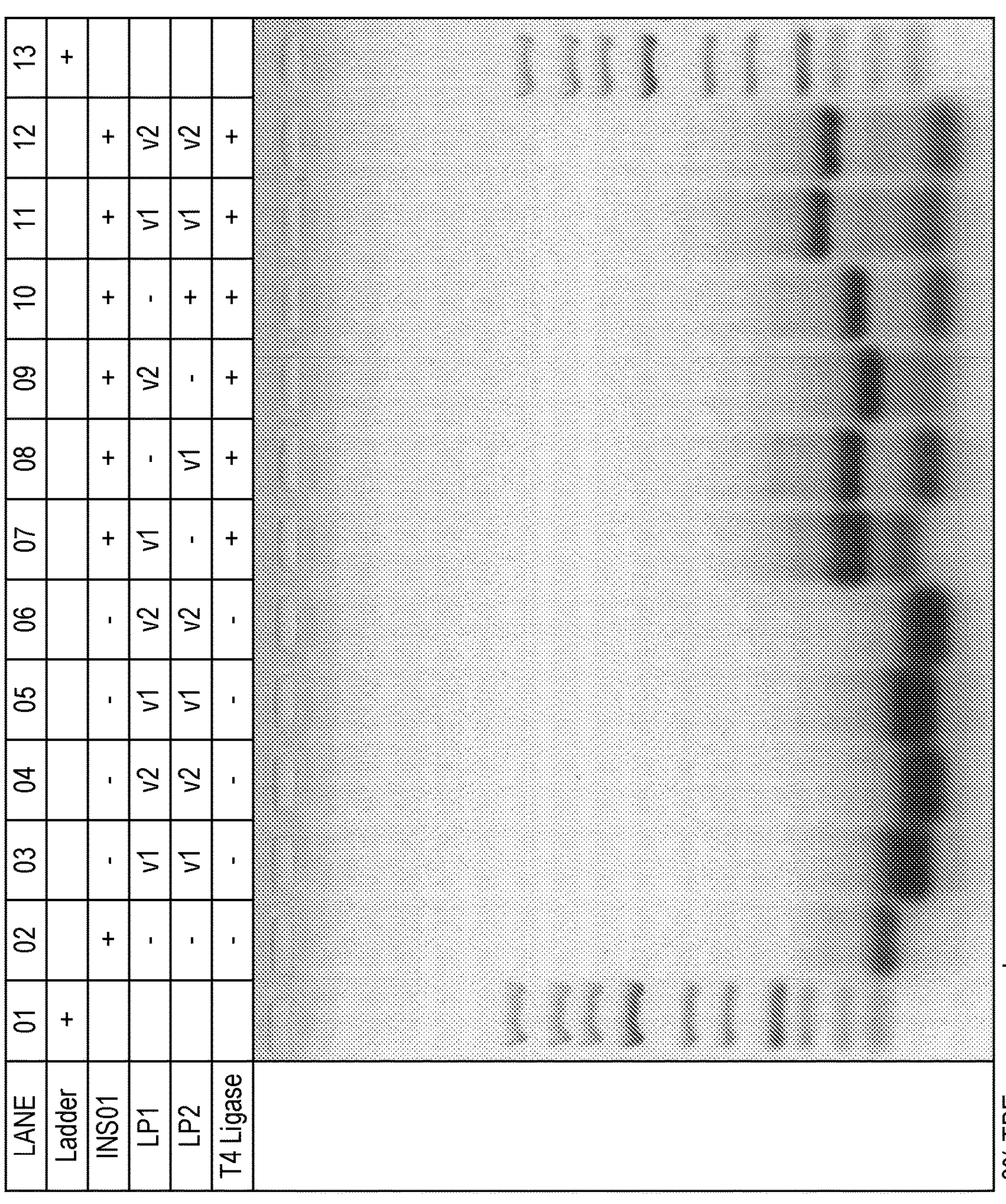
FIG. 13: Non-denaturing agarose gel image shows the INS01 LAMPLate ligation products, the trend in molecular weight shift from adapters-only, monoadapted-INS01 and doubly-adapted-INS01 are clearly observable. Lane 1 and 13 are molecular weight ladders. Lane 2 is insert only. Lane 3-6 are adapter pairs LP1 and LP2 for two designs (v1 and v2) and two concentrations (either 280 pmol L3,4 or 660 pmol L5, 6 per adapter). Lane 7-10 are monoadapter ligations. Lane 11-12 are full ligations for v1 and v2 adapter designs.
Figure 15:
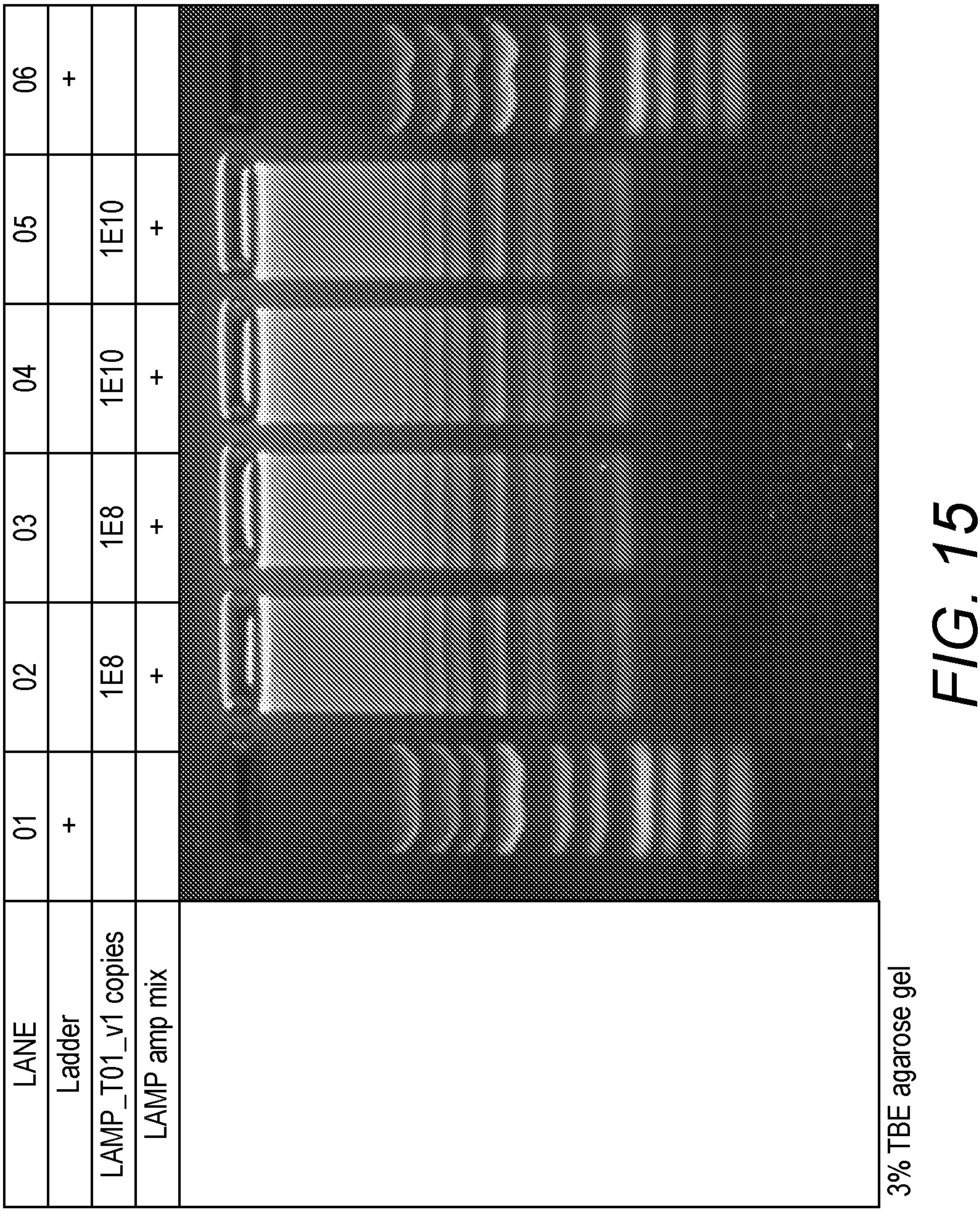
FIG. 15: Non-denaturing agarose gel image shows the pattern of bands typical of LAMP amplified DNA. The ladder of bands of increasing molecular weight is consistent with the tandem repeat concatemer amplification indicative of the method. Lane 1 and 6 are molecular weight ladders. Lane 2-3 and 4-5 are LAMPlicons generated by the solution LAMP amplification of a full length ultramer LAMPlate LAMP_T01_v1 at 1E8 and 1E10 copies respectively.

Example 25 uL solution LAMP amplification reactions were prepared by diluting 12.5 uL of 2× LAMP mastermix (containing buffer, Bst 2.0 WarmStart® DNA Polymerase and dNTPs) with individual ligation-prepared LAMPlate (as described in Example 1, using either v1 or v2 adapter designs and insert SHRK_INS01), LAMP primers LP1_rc_INV_v* (230 μmol, *=v1 or v2) and LP2_INV_v* (230 μmol, *=v1 or v2) and MilliQ water. A range of conditions were tested as outlined in FIG. 4. Reactions were initiated by warming to 65° C. and incubating reactions for 60 minutes. Reactions were either stopped by the addition of 3 uL 500 mM EDTA or purified directly by QIAquick® PCR clean-up columns. Samples were run down a 3% TBE agarose gel stained with gel red stain for visualization.

FIG. 16 legend: Solution LAMP amplification of a single LAMPlate prepared by ligation Non-denaturing agarose gel image shows the pattern of bands typical of LAMP amplification of various single LAMPlicon constructs. The gel clearly shows specificity of amplification. Only full, doubly-ligated LAMPlates support amplification. V1 adapter design seems superior to v2 design. Lane 1, 15 are molecular weight ladders. Lane 2 is SHRK_INS01 inserts-only subjected to solution LAMP amplification reaction. Lane 3, 4 adapter pairs (v1 and v2 respectively) subjected to solution LAMP amplification reaction. Lanes 5,6 are v1-mono-adapted insert subjected to solution LAMP amplification reaction. Lanes 7,8 are v2-mono-adapted insert subjected to solution LAMP amplification reaction. Lanes 9,10 are full, doubly-adapted LAMPlates (v1 and v2 respectively) subjected to solution LAMP amplification reaction. Lanes 11,12 are no-ligase controls for full, doubly-adapted LAMPlates (v1 and v2 respectively) subjected to solution LAMP amplification reaction. Lanes 13, 14 are full, doubly-adapted LAMPlates (v1 and v2 respectively) subjected to solution LAMP amplification reaction using incorrect solution primers (v2 and v1 primers respectively).

Solution LAMP Amplification Using a Pool of Multiple Ligation-Prepared LAMPlates Materials

- LAMPlate inserts (SBL_T01-7)
- LAMP adapters (LP1_v1 and LP2_v1)
- Solution LAMP amplification primers (LP1rc_v1 and LP2_v1)
- Warm start LAMP amplification kit (NEB, E1700S)
- QIAquick® PCR purification columns
- EB buffer (10 mM Tris.HCl pH 8.0)

| Oligos | |
|---|---|
| Oligo name | Sequence (5'-3') |
| LAMP_T01_v1 (SEQ ID NO: 16) | GACTCCTCAGCTAGCGAATGATACGGCGACCACCGACGCTAGCT GAGGAGTCGCTCCATCGGTGTGTACGCGATGGATACCGGCTCAG GCGCAACTTATAGATCCAGTTATCTCGTATGCCGTCTTCTGCTTGA ACTGGATCTATAAG |
| LP1_v1 (SEQ ID NO: 1) | PO4- TCCAGTTATCTCGTATGCCGTCTTCTGCTTGAACTGGATCTATAAG |
| LP2_v1 (SEQ ID NO: 2) | GACTCCTCAGCTAGCGAATGATACGGCGACCACCGACGCTAGCT |
| LP1rc_INV_v1 (SEQ ID NO: 17) | CTTATAGATCCAGTTCAAGCAGAAGACGGCATAC*G*A*G |

-continued

| Oligos | |
|---|---|
| Oligo name | Sequence (5'-3') |
| LP2_INV_v1 (SEQ ID NO: 18) | GACTCCTCAGCTAGCGAATGATACGGCGAC*C*A*C |
| SBL_T01 (SEQ ID NO: 21) | GAGGAGTCTCGCCTTCGTATAGCCTATTACTCGCGTCTAATGGCT CTGAGAGATTCCTCGCCTTAAGGCGAAGATTCAGAAACTGCATAC TTATAGA |
| SBL_T02 (SEQ ID NO: 22) | GAGGAGTCTATCCTCCGTAATCTTAGAATTCGTGTAGAGAGATAG AGGCATTACTCGTTATGCGACAGGACGTCTGAAGCTGTAGAGAGC TTATAGA |
| SBL_T03 (SEQ ID NO: 23) | GAGGAGTCCTAGTACCGGTACTGACTAATGCGCTCGACTAGTATA GCCTCGGCTATGTTCTGCCTCCTATCCTCGCTCATTCGTCTAATCT TATAGA |
| SBL_T04 (SEQ ID NO: 24) | GAGGAGTCGTAAGGACGTATAGCCTATTACTCGCAGCCTCGATAG AGGCATTACTCGTATCCTCTATAGAGGCTCCGCGAACAGCCTCGC TTATAGA |
| SBL_T05 (SEQ ID NO: 25) | GAGGAGTCTTCTGCCCGCCTATCCTTCTCGCGCCCTAGAGTATAG AGGCATTACTCGTGGAGTCCCCTATCCTCGCTCATTTCGACTAGC TTATAGA |
| SBL_T06 (SEQ ID NO: 26) | GAGGAGTCACTGCATCGTATAGCCTATTACTCGTGCCTCTTGGCT CTGAAGCGATAGTTAAGGAGCCTATCCTCGCTCATTTGCCTCTTCT TATAGA |
| SBL_T07 (SEQ ID NO: 27) | GAGGAGTCAGGAGTCCGTATAGCCTATTACTCGGCGTAAGAATAG AGGCATTACTCGTATGCCTACCTATCCTCGCTCATTCCTAGAGTCT TATAGA |

Method

Example 25 uL solution LAMP amplification reactions were prepared by diluting 12.5 uL of 2× LAMP mastermix (containing buffer, Bst2.0 WarmStart® DNA polymerase and dNTPs) with a ligation-prepared LAMPlate pool (as described in Example 1, using LP1_v1 and LP2_v1 adapters and a pool of all seven inserts SBL_T01-7), LAMP primers LP1_rc_INV_v1 (230 μmol) and LP2_INV_v1 (230 μmol) and MilliQ water. A range of conditions were tested as outlined in FIG. 4. Reactions were initiated by warming to 65° C. and incubating reactions for 60 minutes. Reactions were either stopped by the addition of 3 uL 500 mM EDTA or purified directly by QIAquick® PCR clean-up columns. Samples were run down a 3% TBE agarose gel stained with gel red stain for visualization.

FIG. 17 legend: Solution LAMP amplification of a single LAMPlate prepared by ligation Non-denaturing agarose gel image shows the pattern of bands typical of LAMP amplified DNA with various constructs. The gel clearly shows specificity of amplification. Only full, doubly-ligated LAMPlates support amplification. Lane 1, 18, 19 and 30 are molecular weight ladders. Lane 2-8, 20-21 are ssDNA inserts-only subjected to solution LAMP amplification reaction. Lane 9-16 are a serial dilution of the 7-plex ligation-produced LAMPlate pool (1 E7, 1 E8 and 1 E9 copies input) subjected to solution LAMP amplification reaction. Lanes 22,23 are adapters-only subjected to solution LAMP amplification reaction. Lanes 24, 25 are LP1-monoadapted-insert (insert SBL_T01 and SBL-T02 respectively) subjected to solution LAMP amplification reaction. Lanes 26, 27 are LP2-monoadapted-insert (insert SBL_T01 and SBL-T02 respectively) subjected to solution LAMP amplification reaction. Lanes 28, 29 are no ligase controls (insert SBL_T01 and SBL-T02 respectively) subjected to solution LAMP amplification reaction.

The invention claimed is:

1. A method for the surface bound clonal concatameric amplification of a plurality of nucleic acid sequences, comprising:

(a) taking a population of different single-stranded nucleic acid molecules (ss1) of at least 50 nucleotides in length wherein the single strands have a different sequence and each of the single strands has a common hairpin region at the 3' end (LP1) and a common hairpin region at the 5' end (LP2), wherein each hairpin has 5' and 3' hybridising stem arms of between 15-30 base pairs in length, the stem arms having a Tm in the range of 45-55° C.; and (b) clonally amplifying the population of different single-stranded nucleic acid molecules (ss1) using a reaction mixture containing a strand displacing polymerase, nucleotide monomers and amplification primers wherein at least one of the amplification primers (P1) is complementary to at least a portion of the loop of LP1 and to at least a portion of the 5' stem arm of LP1 and one of the amplification primers (P2) hybridizes to at least a portion of a copy of the loop of LP2 (LP2'), wherein in step (b) the amplification primer (P1) is attached to a solid support; and the population of single-stranded nucleic acid molecules are hybridized to the attached amplification primers (P1), such that single strands of different sequences are amplified in physical isolation; and the 3' end of the stem arm of LP1 is extended to make a copy of the single-stranded nucleic acid molecules.

2. The method according to claim 1, wherein in step (b) the 3' end of the stem arm of LP1 is extended to make a complete copy of the single-stranded nucleic acid molecules of at least 50 nucleotides in length (ss1') and a complete copy of sequence LP2 (LP2').

3. The method according to claim 1, wherein the amplification primer P2 is in solution.

4. The method according to claim 1, wherein the presence, absence or sequence of the nucleic acid amplification product is determined.

* * * * *

SEQUENCE LISTING

```
<160> NUMBER OF SEQ ID NOS: 27

<210> SEQ ID NO 1
<211> LENGTH: 46
<212> TYPE: DNA
<213> ORGANISM: Artificial Sequence
<220> FEATURE:
<223> OTHER INFORMATION: LAMP_LP1_v1
<220> FEATURE:
<221> NAME/KEY: misc_difference
<222> LOCATION: (1)..(1)
<223> OTHER INFORMATION: T at position 1 has a PO4 at position 5

<400> SEQUENCE: 1
```

tccagttatc tcgtatgccg tcttctgctt gaactggatc tataag 46

<210> SEQ ID NO 2
<211> LENGTH: 44
<212> TYPE: DNA
<213> ORGANISM: Artificial Sequence
<220> FEATURE:
<223> OTHER INFORMATION: LAMP_LP2_v1

<400> SEQUENCE: 2
gactcctcag ctagcgaatg atacggcgac caccgacgct agct 44

<210> SEQ ID NO 3
<211> LENGTH: 41
<212> TYPE: DNA
<213> ORGANISM: Artificial Sequence
<220> FEATURE:
<223> OTHER INFORMATION: LAMP_LP1_v2
<220> FEATURE:
<221> NAME/KEY: misc_feature
<222> LOCATION: (1)..(1)
<223> OTHER INFORMATION: T at position 1 has a PO4 at position 5

<400> SEQUENCE: 3
tccagttttc agaggatcta gtcggcaact ggatctataa g 41

<210> SEQ ID NO 4
<211> LENGTH: 42
<212> TYPE: DNA
<213> ORGANISM: Artificial Sequence
<220> FEATURE:
<223> OTHER INFORMATION: LAMP_LP2_v2

<400> SEQUENCE: 4
gactcctcag ctagcgcttg gcttcattgt ggtccgctag ct 42

<210> SEQ ID NO 5
<211> LENGTH: 58
<212> TYPE: DNA
<213> ORGANISM: Artificial Sequence
<220> FEATURE:
<223> OTHER INFORMATION: SHRK_INS01
<220> FEATURE:
<221> NAME/KEY: misc_feature
<222> LOCATION: (1)..(1)
<223> OTHER INFORMATION: G at position 1 has a PO4 at position 5

<400> SEQUENCE: 5
gaggagtcgc tccatcggtg tgtacgcgat ggataccggc tcaggcgcaa cttataga 58

<210> SEQ ID NO 6
<211> LENGTH: 72
<212> TYPE: DNA
<213> ORGANISM: Artificial Sequence
<220> FEATURE:
<223> OTHER INFORMATION: SBL_PHIX_01
<220> FEATURE:
<221> NAME/KEY: misc_feature
<222> LOCATION: (1)..(4)
<223> OTHER INFORMATION: G, A, C and T at positions 1, 2, 3 and 4 are linked by phosphorothioate bonds.

<400> SEQUENCE: 6
gactcctcag ctagcgaatg atacggcgac caccgacgct agctgaggag tccaatccgt 60
acgtttccag ac 72

<210> SEQ ID NO 7

<211> LENGTH: 74
<212> TYPE: DNA
<213> ORGANISM: Artificial Sequence
<220> FEATURE:
<223> OTHER INFORMATION: SBL_PHIX_02

<400> SEQUENCE: 7
cttatagatc cagttcaagc agaagacggc atacgagata actggatcta taagacggca 60
gcaataaact caac 74

<210> SEQ ID NO 8
<211> LENGTH: 72
<212> TYPE: DNA
<213> ORGANISM: Artificial Sequence
<220> FEATURE:
<223> OTHER INFORMATION: SBL_PHIX_03
<220> FEATURE:
<221> NAME/KEY: misc_feature
<222> LOCATION: (1)..(4)
<223> OTHER INFORMATION: G, A, C and T at positions 1, 2, 3 and 4 are linked by phosphorothioate bonds.

<400> SEQUENCE: 8
gactcctcag ctagcgaatg atacggcgac caccgacgct agctgaggag tcttaaagcc 60
gctgaattgt tc 72

<210> SEQ ID NO 9
<211> LENGTH: 74
<212> TYPE: DNA
<213> ORGANISM: Artificial Sequence
<220> FEATURE:
<223> OTHER INFORMATION: SBL_PHIX_04

<400> SEQUENCE: 9
cttatagatc cagttcaagc agaagacggc atacgagata actggatcta taagtgcctt 60
tagtacctcg caac 74

<210> SEQ ID NO 10
<211> LENGTH: 72
<212> TYPE: DNA
<213> ORGANISM: Artificial Sequence
<220> FEATURE:
<223> OTHER INFORMATION: SBL_PHIX_05
<220> FEATURE:
<221> NAME/KEY: misc_feature
<222> LOCATION: (1)..(4)
<223> OTHER INFORMATION: G, A, C and T at positions 1, 2, 3 and 4 are linked by phosphorothioate bonds.

<400> SEQUENCE: 10
gactcctcag ctagcgaatg atacggcgac caccgacgct agctgaggag tccgcctact 60
gcgactaaag ag 72

<210> SEQ ID NO 11
<211> LENGTH: 78
<212> TYPE: DNA
<213> ORGANISM: Artificial Sequence
<220> FEATURE:
<223> OTHER INFORMATION: SBL_PHIX_06

<400> SEQUENCE: 11
cttatagatc cagttcaagc agaagacggc atacgagata actggatcta taagaacgat 60
accactgact gaccctca 78

<210> SEQ ID NO 12
<211> LENGTH: 72
<212> TYPE: DNA
<213> ORGANISM: Artificial Sequence
<220> FEATURE:
<223> OTHER INFORMATION: SBL_PHIX_07
<220> FEATURE:
<221> NAME/KEY: misc_feature
<222> LOCATION: (1)..(4)
<223> OTHER INFORMATION: G, A, C and T at positions 1, 2, 3 and 4 are linked by phosphorothioate bonds.

<400> SEQUENCE: 12
gactcctcag ctagcgaatg atacggcgac caccgacgct agctgaggag tccttcttcg 60
gcacctgttt ta 72

<210> SEQ ID NO 13
<211> LENGTH: 74
<212> TYPE: DNA
<213> ORGANISM: Artificial Sequence
<220> FEATURE:
<223> OTHER INFORMATION: SBL_PHIX_08

<400> SEQUENCE: 13
cttatagatc cagttcaagc agaagacggc atacgagata actggatcta taagaaaaat 60
ttagggtcgg catc 74

<210> SEQ ID NO 14
<211> LENGTH: 72
<212> TYPE: DNA
<213> ORGANISM: Artificial Sequence
<220> FEATURE:
<223> OTHER INFORMATION: SBL_PHIX_09
<220> FEATURE:
<221> NAME/KEY: misc_feature
<222> LOCATION: (1)..(4)
<223> OTHER INFORMATION: G, A, C and T at positions 1, 2, 3 and 4 are linked by phosphorothioate bonds.

<400> SEQUENCE: 14
gactcctcag ctagcgaatg atacggcgac caccgacgct agctgaggag tctcaaggtg 60
atgtgcttgc ta 72

<210> SEQ ID NO 15
<211> LENGTH: 74
<212> TYPE: DNA
<213> ORGANISM: Artificial Sequence
<220> FEATURE:
<223> OTHER INFORMATION: SBL_PHIX_10

<400> SEQUENCE: 15
cttatagatc cagttcaagc agaagacggc atacgagata actggatcta taagccaagt 60
ccaaccaaat caag 74

<210> SEQ ID NO 16
<211> LENGTH: 148
<212> TYPE: DNA
<213> ORGANISM: Artificial Sequence
<220> FEATURE:
<223> OTHER INFORMATION: LAMP_T01_v1

<400> SEQUENCE: 16
gactcctcag ctagcgaatg atacggcgac caccgacgct agctgaggag tcgctccatc 60
ggtgtgtacg cgatggatac cggctcaggc gcaacttata gatccagtta tctcgtatgc 120
cgtcttctgc ttgaactgga tctataag 148

<210> SEQ ID NO 17
<211> LENGTH: 37
<212> TYPE: DNA
<213> ORGANISM: Artificial Sequence
<220> FEATURE:
<223> OTHER INFORMATION: LP1rc_INV_v1
<220> FEATURE:
<221> NAME/KEY: misc_feature
<222> LOCATION: (34)..(37)
<223> OTHER INFORMATION: C, G, A and G at positions 34, 35, 36 and 37 are linked by phosphorothioate bonds.

<400> SEQUENCE: 17
cttatagatc cagttcaagc agaagacggc atacgag 37

<210> SEQ ID NO 18
<211> LENGTH: 33
<212> TYPE: DNA
<213> ORGANISM: Artificial Sequence
<220> FEATURE:
<223> OTHER INFORMATION: LP2_INV_v1
<220> FEATURE:
<221> NAME/KEY: misc_feature
<222> LOCATION: (30)..(33)
<223> OTHER INFORMATION: C, C, A and C at positions 30, 31, 32 and 33 are linked by phosphorothioate bonds.

<400> SEQUENCE: 18
gactcctcag ctagcgaatg atacggcgac cac 33

<210> SEQ ID NO 19
<211> LENGTH: 32
<212> TYPE: DNA
<213> ORGANISM: Artificial Sequence
<220> FEATURE:
<223> OTHER INFORMATION: LP1rc_INV_v2
<220> FEATURE:
<221> NAME/KEY: misc_feature
<222> LOCATION: (29)..(32)
<223> OTHER INFORMATION: T, C, T and G at positions 29, 30, 31 and 32 are linked by phosphorothioate bonds.

<400> SEQUENCE: 19
cttatagatc cagttgccga ctagatcctc tg 32

<210> SEQ ID NO 20
<211> LENGTH: 32
<212> TYPE: DNA
<213> ORGANISM: Artificial Sequence
<220> FEATURE:
<223> OTHER INFORMATION: LP2_INV_v2
<220> FEATURE:
<221> NAME/KEY: misc_feature
<222> LOCATION: (29)..(32)
<223> OTHER INFORMATION: G, T, G and G at positions 29, 30, 31 and 32 are linked by phosphorothioate bonds.

<400> SEQUENCE: 20
gactcctcag ctagcgcttg gcttcattgt gg 32

<210> SEQ ID NO 21
<211> LENGTH: 97
<212> TYPE: DNA
<213> ORGANISM: Artificial Sequence
<220> FEATURE:
<223> OTHER INFORMATION: SBL_T01

<400> SEQUENCE: 21
gaggagtctc gccttcgtat agcctattac tcgcgtctaa tggctctgag agattcctcg 60
ccttaaggcg aagattcaga aactgcatac ttataga 97

<210> SEQ ID NO 22
<211> LENGTH: 97
<212> TYPE: DNA
<213> ORGANISM: Artificial Sequence
<220> FEATURE:
<223> OTHER INFORMATION: SBL_T02

<400> SEQUENCE: 22
gaggagtcta tcctccgtaa tcttagaatt cgtgtagaga gatagaggca ttactcgtta 60
tgcgacagga cgtctgaagc tgtagagagc ttataga 97

<210> SEQ ID NO 23
<211> LENGTH: 97
<212> TYPE: DNA
<213> ORGANISM: Artificial Sequence
<220> FEATURE:
<223> OTHER INFORMATION: SBL_T03

<400> SEQUENCE: 23
gaggagtcct agtaccggta ctgactaatg cgctcgacta gtatagcctc ggctatgttc 60
tgcctcctat cctcgctcat tcgtctaatc ttataga 97

<210> SEQ ID NO 24
<211> LENGTH: 97
<212> TYPE: DNA
<213> ORGANISM: Artificial Sequence
<220> FEATURE:
<223> OTHER INFORMATION: SBL_T04

<400> SEQUENCE: 24
gaggagtcgt aaggacgtat agcctattac tcgcagcctc gatagaggca ttactcgtat 60
cctctataga ggctccgcga acagcctcgc ttataga 97

<210> SEQ ID NO 25
<211> LENGTH: 97
<212> TYPE: DNA
<213> ORGANISM: Artificial Sequence
<220> FEATURE:
<223> OTHER INFORMATION: SBL_T05

<400> SEQUENCE: 25
gaggagtctt ctgcccgcct atccttctcg cgccctagag tatagaggca ttactcgtgg 60
agtcccctat cctcgctcat ttcgactagc ttataga 97

<210> SEQ ID NO 26
<211> LENGTH: 97
<212> TYPE: DNA
<213> ORGANISM: Artificial Sequence
<220> FEATURE:
<223> OTHER INFORMATION: SBL_T06

<400> SEQUENCE: 26
gaggagtcac tgcatcgtat agcctattac tcgtgcctct tggctctgaa gcgatagtta 60
aggagcctat cctcgctcat ttgcctcttc ttataga 97

<210> SEQ ID NO 27
<211> LENGTH: 97
<212> TYPE: DNA

-continued

```
<213> ORGANISM: Artificial Sequence
<220> FEATURE:
<223> OTHER INFORMATION: SBL_T07

<400> SEQUENCE: 27

gaggagtcag gagtccgtat agcctattac tcggcgtaag aatagaggca ttactcgtat     60

gcctacctat cctcgctcat tcctagagtc ttataga                              97
```